(12) United States Patent
Brennan et al.

(10) Patent No.: US 10,166,402 B2
(45) Date of Patent: Jan. 1, 2019

(54) VISIBLE LIGHT PHOTO-DISINFECTION PATCH

(71) Applicant: Excelitas Technologies Corp., Waltham, MA (US)

(72) Inventors: Kevin Brennan, Villa Park, IL (US); Thomas Papanek, Lake Forest, IL (US)

(73) Assignee: Excelitas Technologies Corp., Waltham, MA (US)

( * ) Notice: Subject to any disclaimer, the term of this patent is extended or adjusted under 35 U.S.C. 154(b) by 406 days.

(21) Appl. No.: 13/895,943

(22) Filed: May 16, 2013

(65) Prior Publication Data
US 2014/0343478 A1 Nov. 20, 2014

(51) Int. Cl.
*A61B 5/06* (2006.01)
*A61N 5/06* (2006.01)
*A61F 13/00* (2006.01)
*A61L 2/00* (2006.01)
*F21V 8/00* (2006.01)

(52) U.S. Cl.
CPC ...... *A61N 5/0624* (2013.01); *A61F 13/00068* (2013.01); *A61L 2/0052* (2013.01); *G02B 6/001* (2013.01); *Y10T 29/49826* (2015.01)

(58) Field of Classification Search
CPC ..... A61N 5/0624; G02B 6/001; A61L 2/0052; A61L 2/0058; A61L 2/0047; A61F 2013/00182; A61F 13/00
USPC .......................................................... 607/88
See application file for complete search history.

(56) References Cited

U.S. PATENT DOCUMENTS

| | | |
|---|---|---|
| 4,172,631 A | 10/1979 | Yevick et al. |
| 4,229,783 A | 10/1980 | Eberhardt |
| 4,234,907 A | 11/1980 | Daniel |
| 4,455,597 A | 6/1984 | Vukasovic |
| 4,519,017 A | 5/1985 | Daniel |
| 4,714,983 A | 12/1987 | Lang |
| 4,761,047 A | 8/1988 | Mori |
| 4,765,701 A | 8/1988 | Cheslak |

(Continued)

FOREIGN PATENT DOCUMENTS

| | | |
|---|---|---|
| WO | WO 01/14012 A1 | 3/2001 |
| WO | WO2006081221 A2 | 8/2006 |

(Continued)

OTHER PUBLICATIONS

International Search Report for pct/us14/038048, dated Aug. 21, 2014.

(Continued)

*Primary Examiner* — Aaron Roane
(74) *Attorney, Agent, or Firm* — Peter A. Nieves; Sheehan Phinney Bass & Green PA

(57) ABSTRACT

A method and device are presented for providing patient safe light to a wound. The device includes a radiation source producing flora lethal radiation wavelengths, a radiation conduit detachably optically coupled to the radiation source, and a patch remotely located from the radiation source configured to at least partially conform to a surface contour of the wound. The patch includes a flexible panel formed of a radiation transmitting material able to withstand sterilization, including at least one surface with a disturbed surface area configured to emit radiation upon the wound.

29 Claims, 16 Drawing Sheets

(56) References Cited

U.S. PATENT DOCUMENTS

| | | |
|---|---|---|
| 4,790,752 A | 12/1988 | Cheslak |
| 4,802,066 A | 1/1989 | Mori |
| 4,885,663 A | 12/1989 | Parker |
| 4,907,132 A | 3/1990 | Parker |
| 4,918,577 A | 4/1990 | Furudate |
| 4,929,062 A | 5/1990 | Guzik |
| 5,005,108 A * | 4/1991 | Pristash ............... G02B 6/0005 362/23.15 |
| 5,040,098 A | 8/1991 | Tanaka |
| 5,042,900 A | 8/1991 | Parker |
| 5,097,396 A | 3/1992 | Myers |
| 5,138,480 A | 8/1992 | Pristash |
| 5,202,950 A | 4/1993 | Arego |
| 5,226,105 A | 7/1993 | Myers |
| 5,249,105 A | 9/1993 | Koizumi |
| 5,295,216 A | 3/1994 | Halter |
| 5,303,323 A | 4/1994 | Mezei |
| 5,307,245 A | 4/1994 | Myers |
| 5,312,569 A | 5/1994 | Mezei |
| 5,312,570 A | 5/1994 | Halter |
| 5,499,912 A | 3/1996 | Mezei |
| 5,514,126 A | 5/1996 | Prescott |
| 5,568,964 A | 10/1996 | Parker |
| 5,655,827 A | 8/1997 | Kaneko |
| 5,838,403 A | 11/1998 | Jannson |
| 5,894,686 A | 4/1999 | Parker |
| 5,907,222 A | 5/1999 | Lengyl |
| 5,975,711 A | 11/1999 | Parker |
| 6,030,089 A | 2/2000 | Parker |
| 6,079,838 A | 6/2000 | Parker |
| 6,096,066 A | 8/2000 | Chen |
| 6,123,431 A | 9/2000 | Teragaki |
| 6,158,867 A | 12/2000 | Parker |
| 6,290,713 B1 | 9/2001 | Russell |
| 6,416,390 B1 | 7/2002 | Mezei |
| 6,443,978 B1 | 9/2002 | Zharov |
| 6,591,049 B2 | 7/2003 | Williams |
| 6,705,193 B2 | 3/2004 | Koizumi |
| 6,733,187 B2 | 5/2004 | Page |
| 6,872,220 B2 | 2/2005 | Williams |
| 6,861,609 B2 | 3/2005 | Schulz |
| 6,874,925 B2 | 4/2005 | Page |
| 6,922,519 B2 | 5/2005 | Page |
| 6,910,783 B2 | 6/2005 | Mezei |
| 7,147,663 B1 | 12/2006 | Williams |
| 7,163,326 B2 | 1/2007 | Cassarly |
| 7,234,853 B2 * | 6/2007 | Givoletti ............... D02G 3/441 160/10 |
| 7,304,201 B2 | 12/2007 | Holloway |
| 7,305,163 B2 | 12/2007 | Williams |
| 7,306,559 B2 | 12/2007 | Williams |
| 8,167,461 B2 | 5/2012 | Nichol |
| 8,215,314 B2 | 7/2012 | Chan |
| 2001/0047144 A1 | 11/2001 | Tillotson |
| 2002/0143373 A1 | 10/2002 | Courtnage |
| 2004/0010299 A1 | 1/2004 | Tolkoff |
| 2004/0166146 A1 | 8/2004 | Holloway |
| 2004/0193218 A1 | 9/2004 | Butler |
| 2005/0080465 A1 | 4/2005 | Zelickson |
| 2007/0208395 A1 | 9/2007 | Leclerc |
| 2007/0233208 A1 | 10/2007 | Kurtz |
| 2010/0121252 A1 | 5/2010 | Keltner |
| 2010/0179469 A1 | 7/2010 | Hammond |
| 2010/0214786 A1 | 8/2010 | Nichol |
| 2010/0256541 A1 | 10/2010 | Pryor |
| 2011/0176326 A1 * | 7/2011 | Stephan ............... G02B 6/0008 362/555 |
| 2012/0116485 A1 | 5/2012 | Burgmann |
| 2012/0165716 A1 | 6/2012 | Reuben |
| 2012/0201049 A1 | 8/2012 | Sherman |
| 2013/0035629 A1 | 2/2013 | Soltz |
| 2014/0221763 A1 * | 8/2014 | Vayser ............... A61B 90/30 600/245 |

FOREIGN PATENT DOCUMENTS

| | | |
|---|---|---|
| WO | WO2010151563 A1 | 12/2010 |
| WO | WO 2011082420 A1 | 7/2011 |

OTHER PUBLICATIONS

NATUS Medical Incorporated, 1501 Industrial Road, San Carlos CA 94070 USA, www.natus.com, neoBLUE blanket LED Phototherapy flyer, DOC-004920B, Sep. 2012.

GE Healthcare, PO Box 900, FIN-00031 GE, Finland, www.gehealthcare.com, BiliSoft LED Phototherapy System, 2037512-002-2007.09-V1.0.

Lumitex, Inc., 8443 Dow Circle, Strongsville, OH 44136, www.lumitex.com, Woven Fiber Optics; http://www.lumitex.com/medical-devices/technologies/woven-fiber-optic, printed May 16, 2013.

NOBIS, LLC; 450nm Devices and 470 nm Devices, NOBISBLUE.com, Sep. 2012.

Lumitex, Inc., 8443 Dow Circle, Strongsville, OH 44136, www.lumitex.com, UniGlo®; http://www.lumitex.com/medical-devices/technologies/uni-glo, printed May 16, 2013.

Lumitex, Inc., 8443 Dow Circle, Strongsville, OH 44136, www.lumitex.com; Clad Flat Fiber™; http://www.lumitex.com/electronics-backlighting/technologies/flat-fiber; printed May 16, 2013.

* cited by examiner

VISIBLE LIGHT PHOTO-DISINFECTION PATCH

FIELD OF THE INVENTION

The present invention relates to medical devices, and more particularly, is related to a wound disinfection device.

BACKGROUND OF THE INVENTION

The Centers for Disease Control and Prevention has estimated that 1.7 million nosocomial infections occur annually in the U.S. with 99,000 associated deaths. The reduction of such infections forms an important component of efforts to improve healthcare safety. Many of these infections originate from "natural flora" bacteria or fungi that have developed immunity to traditional disinfection and antibiotic regimens. Research has shown that relevant infectious flora demonstrate significant susceptibility to select wavelengths of visible light in the presence of oxygen and can be substantially reduced with practical exposure powers and time. Methods for preventing/reducing infections are needed due to the increased flora resistance to antibiotic and conventional disinfection.

Several types of patients are at risk of infection. There is a high correlation of surgical patients with nosocomial infections. Compromised skin due to implant, surgical, catheter or needle penetration and subsequent covering of the resultant wound with light-blocking bandages provides a high-risk vector site for infection by light-sensitive pathogenic microbes, such as Methicillin-resistant *Staphylococcus aureus* (MRSA). Other types of wounds at high risk for infection include, for example, burns, and chronic diabetic ulcers, among others.

Prior art devices implementing the medicinal use of light on skin include multiple light and/or radiation emitting sources and associated electrical connectivity incorporated into a bandage or other material directly at the site of the wound. These are problematic for application to a fresh or chronic open wound site. Such devices lack provisions for the required sterility. In particular, organic light emitting diodes (OLED) are subject to degradation when exposed to sterilizing agents, such as gamma radiation, steam or Ethylene Oxide. Incorporating light sources directly into the bandage material is cost prohibitive, and ill-suited for a disposable bandage. In addition, the proximity of the light/radiation emitters to the wound presents a challenge to conducting heat generated by the light/radiation emitters away from the patient. Further, locating OLEDs in the proximity of the wound may be problematic as OLEDs generally have a reduced service life in high humidity conditions.

The wiring used for electrical connectivity between the light/radiation emitters and a power source present risks such as exposing the patient to electrically energized components and to electromagnetic fields, which may be of particular concern to surgical patients with other electromechanical medical devices, such as pace makers. Supplemental oxygen used in adjunct medical therapy may further be susceptible to ignition. By using a lightguide to move the radiation emitter remote from the patient these concerns can be addressed.

Lightguides include physical media that conveys light introduced to an ingress portion of the media to an egress portion of the media some distance apart from the ingress portion. The physical media is an optically conducting media such as a clear glass or plastic. A common optically conducting media is an optical fiber. Another form of lightguide is a transparent plate or film, where the ingress and/or egress portion is an edge of the plate of film. Such a lightguide is called an edge lit film.

When light traveling in an optically conducting medium reaches a boundary having an angle larger than the critical angle for the boundary, the light is completely reflected. This is called total internal reflection (TIR). The TIR of an optical fiber confines light within the optical fiber. Light travels through the fiber, bouncing back and forth off the boundary between the fiber and fiber surface. Only light that enters the fiber within a certain range of angles can travel down the fiber without escaping. Disturbing the surface of a fiber creates a region where some of the conducted light escapes the fiber. These areas are called dispersion areas.

Similarly, the TIR of an edge lit film confines light within the edge lit film. The TIR of the edge lit film may be disturbed in several ways, for example, bending the film beyond a TIR threshold, or disturbing the surface of the edge lit film by several methods, including scoring or laminating a substance with different optical properties. An edge lit film may not emit any visible light from its planar surface if that planar surface is not disturbed. For example, a substantially transparent edge lit film may appear transparent and unlit even when conducting light through it if the planar surface is not disturbed.

Flexible light producing films have been used in several applications, for example, back illumination for displays and control panels. FIG. 1A shows a first prior art flexible light producing panel 1 formed by assembling many individual optical fibers together into an aligned sheet. A group 10 of individual fibers extends from the panel, and is bundled into a light cable 11 formed of the individual fibers. The light cable 11 is attached to a light source 14 by a connector 12. The light cable 11 conveys light from the light source 14 to the light panel 1.

As shown by FIG. 1B, individual optical fibers 5 may be interleaved, for example, woven, to form one or more thin light emitting layers 3,4 of a light producing panel. Alternatively, individual fibers 5 may be aligned substantially in parallel.

As shown by FIG. 1C, The planar surface 2 of the light emitting panel 1 may be disrupted, for example by scoring the planar surface, to cause light to be emitted from the disrupted surface of the fibers rather than being transmitted to the end of each fiber. However, the process of forming a large number of individual fiber optic strands into a panel is complex and costly.

A second prior art light producing panel or film is formed from a single sheet of edge lit light conducting material having a TIR so that it contains and conducts light in a fashion similar to a fiber optic cable. Light may be dispersed from the surface of the panel by disturbing the surface of the panel, similarly to the light fibers described above and shown in FIG. 1C. Light may be introduced into the panel through the edge of the panel, for example, by abutting a light source against the edge of the panel. In instances where it is advantageous to locate the panel apart from the light source, a light guide, such as one or more fiber optic strands may be used to convey the light from the light source to the panel. Each of the light guides is affixed to the edge of the panel, for example, by an adhesive or bonding agent. However, joining the light guide to the light panel may be difficult, costly, and lose light in the transfer from the light guide to the panel. Therefore, there is a need in the industry to overcome one or more of the above shortcomings.

SUMMARY OF THE INVENTION

Embodiments of the present invention provide a visible light photo-disinfection patch. Briefly described, the present invention is directed to device providing patient safe light to a wound from a radiation source producing flora lethal radiation wavelengths. The device includes a radiation conduit optically coupled to the radiation source including a radiation ingress portion and a radiation egress portion conveying the floral lethal radiation from the radiation source, wherein the radiation conduit does not substantially convey heat generated by the radiation source, and a patch remotely located from the radiation source and optically coupled to the radiation conduit. The patch is configured to at least partially conform to a surface contour of the wound, and includes a flexible panel formed of a radiation transmitting material able to withstand sterilization, the panel having a first planar surface and a second planar surface, wherein at least one of the first planar surface and the second planar surface having a disturbed surface area configured to emit radiation received from the radiation conduit egress portion upon the wound.

A second aspect of the present invention is directed to a method for manufacturing a flexible light transmitting panel. The method includes the steps of forming a sheet of light transmitting material having a skiving region and an emitting region, forming a plurality of fibers from the skiving region, and forming an area of surface disruption on a first surface of the emitting region.

A third aspect of the present invention is directed to a negative pressure wound therapy device providing patient safe light to a wound from a radiation source producing flora lethal radiation wavelengths. The device includes a radiation conduit optically coupled to the radiation source comprising a radiation ingress portion and a radiation egress portion conveying the floral lethal radiation from the radiation source. The radiation conduit does not substantially convey heat generated by the radiation source. The device includes a patch remotely located from the radiation source and optically coupled to the radiation conduit, configured to at least partially conform to a surface contour of the wound. The wound includes a vacuum permeable flexible panel formed of a radiation transmitting material able to withstand sterilization, the panel comprising a first planar surface and a second planar surface, wherein at least one of the first planar surface and the second planar surface comprises a disturbed surface area configured to emit radiation received from the radiation conduit egress portion upon the wound.

Briefly described in architecture, a fourth aspect of the present invention is directed to a system providing patient safe light to a wound. The system includes a radiation source producing flora lethal radiation wavelengths, a radiation conduit optically coupled to the radiation source including a radiation ingress portion and a radiation egress portion conveying the floral lethal radiation from the radiation source, wherein the radiation conduit does not substantially convey heat generated by the radiation source, and a patch remotely located from the radiation source and optically coupled to the radiation conduit. The patch is configured to at least partially conform to a surface contour of the wound, and includes a flexible panel formed of a radiation transmitting material able to withstand sterilization, the panel having a first planar surface and a second planar surface, wherein at least one of the first planar surface and the second planar surface having a disturbed surface area configured to emit radiation received from the radiation conduit egress portion upon the wound.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principals of the invention.

DETAILED DESCRIPTION

Figure 1A:
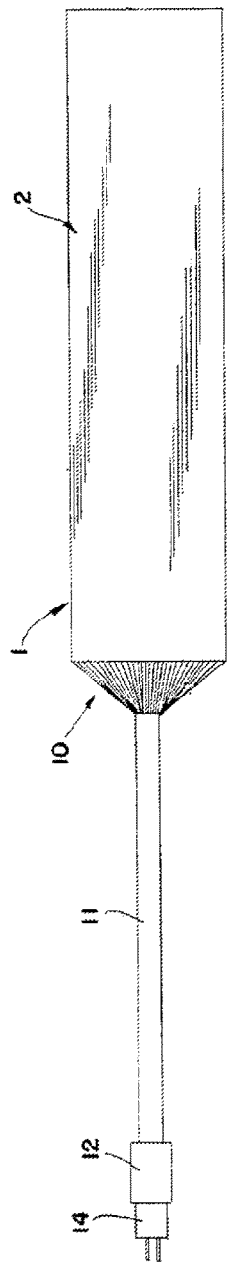
FIG. 1A is a schematic diagram of a prior art optic panel.
Figure 1B:
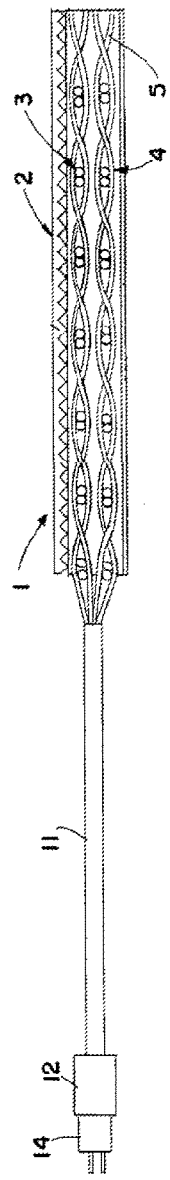
FIG. 1B is a schematic diagram of a prior art optic panel side cross section.

Reference will now be made in detail to embodiments of the present invention, examples of which are illustrated in the accompanying drawings. Wherever possible, the same reference numbers are used in the drawings and the description to refer to the same or like parts.

The following definitions are useful for interpreting terms applied to features of the embodiments disclosed herein, and are meant only to define elements within the disclosure. No limitations on terms used within the claims are intended, or should be derived, thereby. Terms used within the appended claims should only be limited by their customary meaning within the applicable arts.

As used within this disclosure, radiation refers to electromagnetic radiation having wavelengths both within and outside of the visible spectrum.

As used within this disclosure, a Negative Pressure Wound Therapy (NPWT) device refers to a specialized bandage, for example, with a vacuum pump, causing blood to come to the surface of a wound.

As used within this disclosure, skiving means slitting, or cutting, a portion of a flat panel of material into approximately parallel strips of material; while leaving the strips attached and contiguous with the flat panel. The slitting or cutting maybe performed by multiple conventional means such as with knives, rotary cutting wheels, laser, water jet etc.

As used within this disclosure, open-cell foam refers to a fluid bearing material, for example, but not limited to sponge, foam, and gauze.

As used within this disclosure, vacuum permeable refers to a material permeable such that a fluid may pass through the material when drawn by a vacuum or negative pressure. Such a material many have a single perforation or multiple perforations.

Exemplary embodiments are described of a device providing flora lethal, patient safe light to a wound site via a flexible, sterile, gas permeable, disposable patch detachably optically coupled to a non-disposable, non-sterile remote light source in order to deny wound site colonization of light sensitive flora and possible subsequent infection. The device provides this light without light wavelengths known to induce detrimental effects on skin tissue, or unproductive thermal energy that would harm or discomfort the patient. The device is of sufficient simplicity of construction to allow for conventional sterile manufacture and disposable use, including a laminate of a transparent gas permeable biocompatible diffuser mechanically attached to a light transmitting panel.

Figure 2:
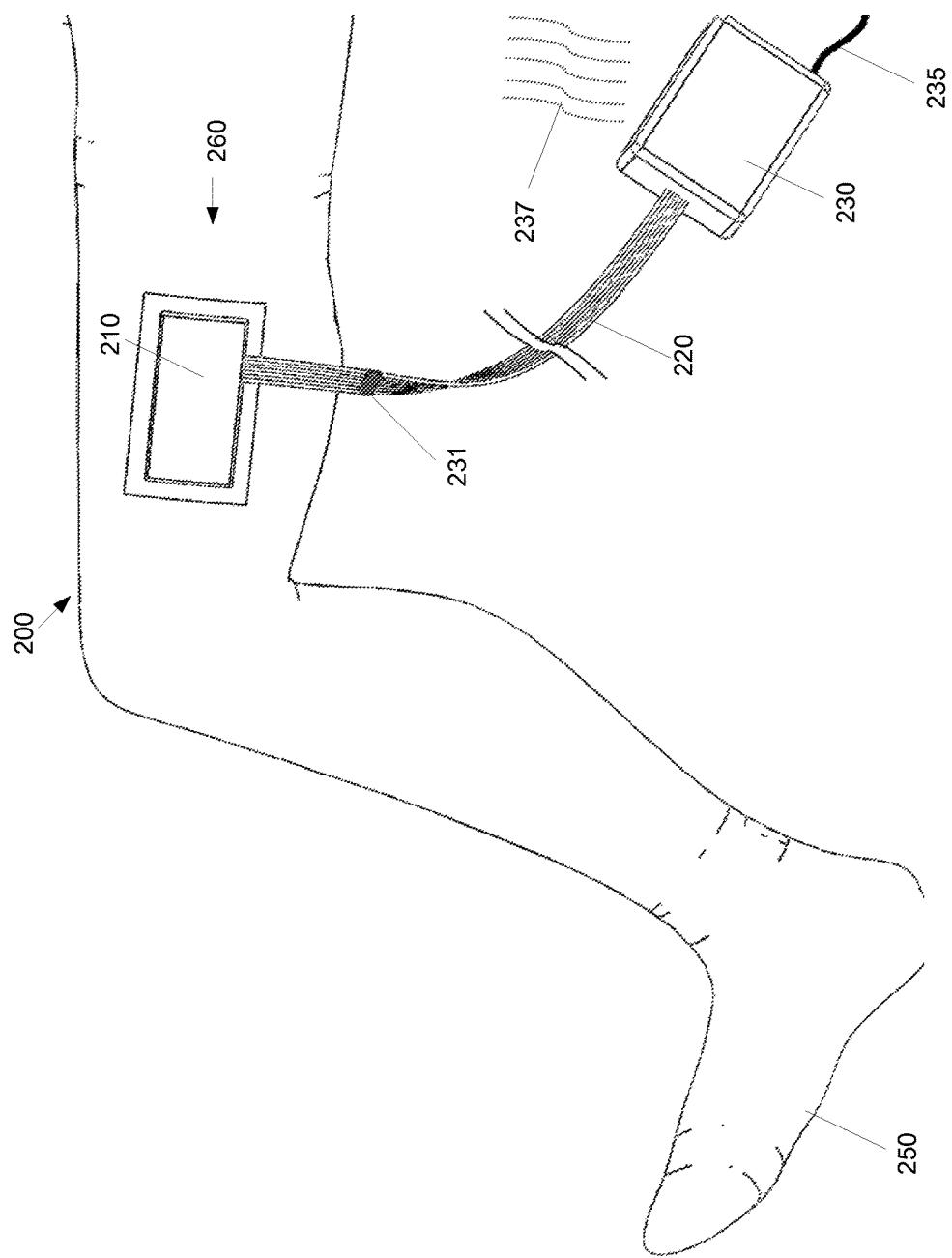
FIG. 2 is a schematic diagram of a first embodiment of a visible light photo-disinfection patch, conduit and light source.

FIG. 2 shows an exemplary first embodiment of a visible light photo-disinfection patch system 200. The system 200 includes a light source 230, or radiation source, a light/radiation conduit 220, and a patch 210. The light source 230 produces light that is conveyed by the light conduit 220 to the patch 210, where the patch 210 emits the conveyed light in the proximity of a wound 260 of a patient 250.

The light source 230 produces flora lethal, patient safe light/radiation with one or more light producing elements, for example, LEDs. The light source 230 may include an internal power source, for example, one or more chemical batteries, or receive power from an external power source, for example via a power line 235. The light source may produce thermal emissions 237, and therefore it may be desirable to position the light source remotely from a patient 250. The light source 230 produces light that is introduced to an ingress end of the light/radiation conduit 220. The light conduit 220 is formed of a light conveying material, for example, polycarbonate, that conveys light produced by the light source 230, but does not substantially convey thermal emissions 237 from the light source 230. The light conduit 220 may be detachably connected to the light source 230, for example with an optical coupling 231, such that the light source may be easily replaced, for example, by a light source producing different light wavelengths or intensities. The detachability of the light conduit 220 also facilitates sterilization of the light conduit 220 and/or the patch 210 independent of the light source 230. The patch 210 and/or the conduit 220 may be sterilized using any of several methods, for example, but not limited to, gamma radiation, steam, Ethylene Oxide, peroxide, and ultraviolet radiation, among others.

The optical coupling 231 provides mechanical attachment and detachment between segments of one or more optical conduits, as known to persons having ordinary skill in the art. The optical coupling 231 may be implemented at any location along the optical conduit between light source 230 and patch 210. There may also be multiple optical couplings 231, for example, a first optical coupling (not shown) near to the light source 230 and a second optical coupling 231 near to the patch 210 to allow different lengths of conduit 220 and easy dis-connection and sterilization of the conduit 220.

Figure 1C:
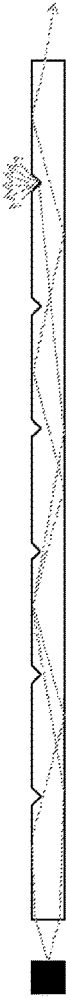
FIG. 1C is a schematic diagram of a prior art optic fiber and/or panel side cross section, indicating light emitting from surface disruptions.

An egress end of the light conduit 220 is attached to the patch 210. The patch 210 contains a flexible panel, for example, but not limited to a polycarbonate edge lit film. At least one planar surface of the flexible panel is disturbed (see FIG. 1C), so that light received from the light source 230 via the light conduit 220 is emitted in the vicinity of the wound 260 of the patient 250. Embodiments of the light source 230, the light conduit 220, and the flexible panel of the patch 210 are described in greater detail below.

An exemplary embodiment of a flexible panel of a photo-disinfection patch 210 is formed of a one-piece integral light emission area contiguously attached to a light conduit 220 made up of a plurality of optic fibers, where the optic fibers are skived from the sheet of material forming the light emission area. The fibers may be bundled together and paired with one or more light sources providing flora lethal, patent safe radiation/light. The light conduit 220 conveys the light from the one or more light sources 230 to the emission area in the patch 210, where the light is dispersed through surface disruptions formed on the flexible panel of the patch 210.

Figure 3A:
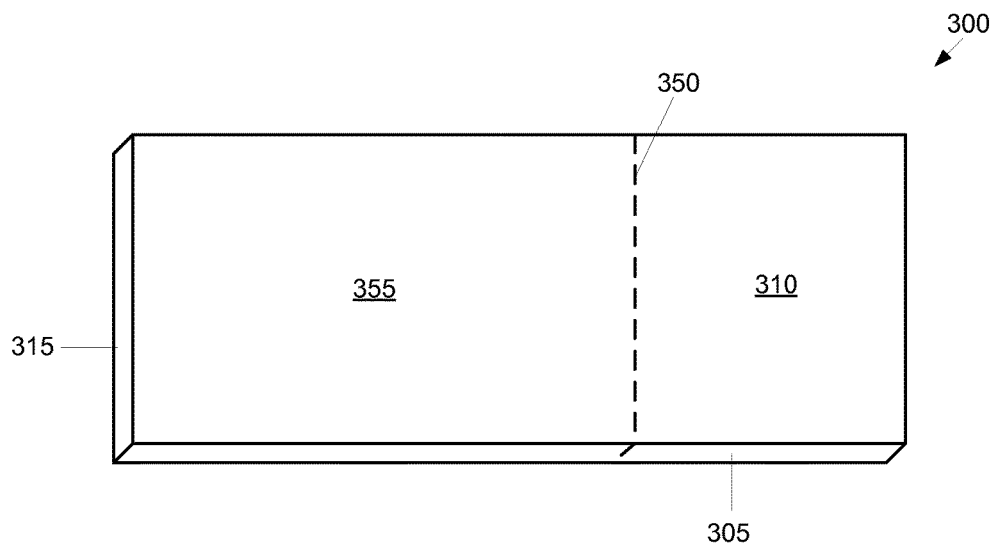
FIGS. 3A, 3B, and 3C are schematic diagrams of a simplified view of a first embodiment of a flexible optic patch.

FIG. 3A shows a first exemplary embodiment of a flexible panel 300. As shown by FIG. 3A, a thin sheet 305 or film of light transmitting material (lightguide) is provided. The sheet may generally have a TIR such that light transmitted into an edge 315 of the sheet 305 is propagated through the sheet 305, but not dispersing through the flat face of the sheet 305. The sheet 305 may be partitioned into a panel portion 310 and a skiving portion 355, where the dashed line 350 indicates the partition line between the panel portion 310 and the skiving portion 355.

Figure 3B:
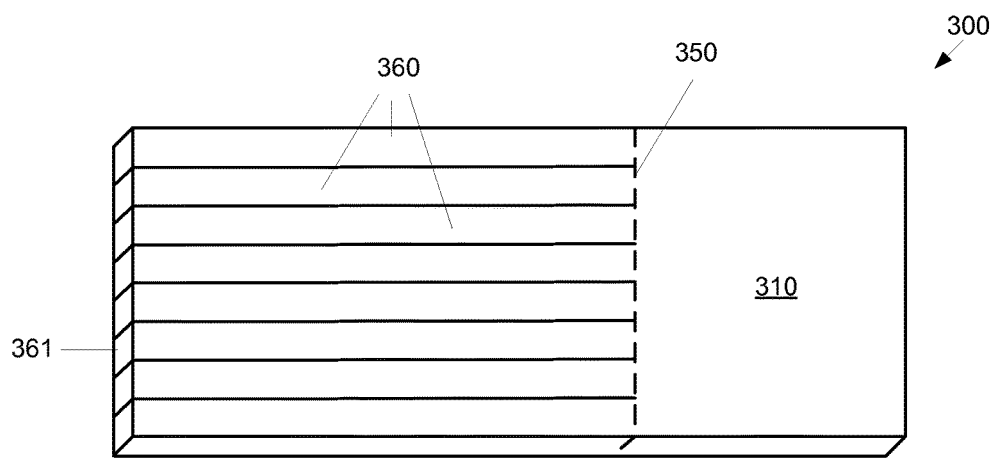

FIG. 3B shows the sheet 305 of the panel 300 after skiving. The skiving portion 355 of the sheet may be skived into a plurality of fibrous appendages 360, where each individual fibrous appendage 360 functions as an optical light guide, such that each of the fibrous appendages 360 has substantially the same TIR as the sheet 355 before skiving. Light transmitted through an end 361 of a fibrous appendage 360 may be transmitted through the fibrous appendage 360 past the partition 350 and into the panel portion 310. It should be noted that the partition 350 is only a demarcation line, and that the material of each fibrous appendage 360 is substantially contiguous with the adjacent portion of the panel portion 310 across the partition 350. While the partition 350 is depicted by FIG. 3B as a substantially straight line, there is no objection to a partition having other shapes, for example, a curve line or an uneven line. It should further be noted that the thickness of the sheet and the size of the fibrous appendages are exaggerated in FIGS. 3A and 3B for clarity.

Figure 3C:
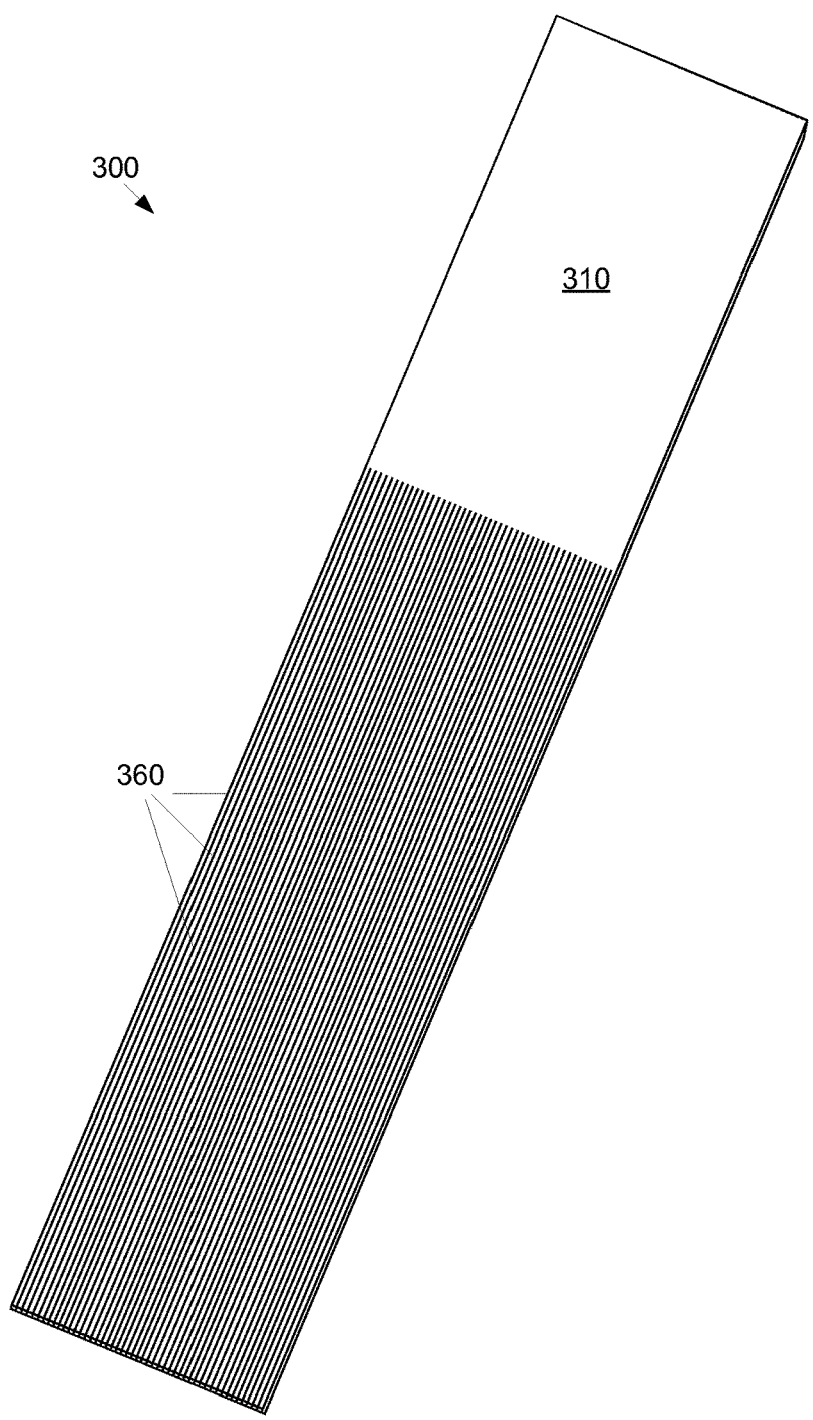

FIG. 3C shows a flexible thin film optic device with a higher density of fibrous appendages 360 relative to the panel 310. The length of the fibrous appendages 360 may be longer or shorter relative to the size of the panel portion 310. The fibrous appendages 360 as shown by FIG. 3C are each substantially the same length. However, there is no objection to individual fibrous appendages 360 being of different lengths. For example, if the fibrous appendages are bundled together, it may be advantageous for individual strands at the center to be somewhat shorter than strands at the end such that the ends of the strands at the end of the bundle are substantially coplanar. In another example, a first group of strands may be routed to a first destination and a second group of strands may be routed to a second destination, where the first destination is closer to the panel 310 than the second destination, so the strands in the first group may advantageously be shorter than the strands in the second group.

While the above description describes the individual fibrous appendage strands 360 being skived from a single sheet of light transmitting material 305, there is no objection to forming the fibrous appendages 360 and the panel portion 310 concurrently, for example in a mold.

Figure 4A:
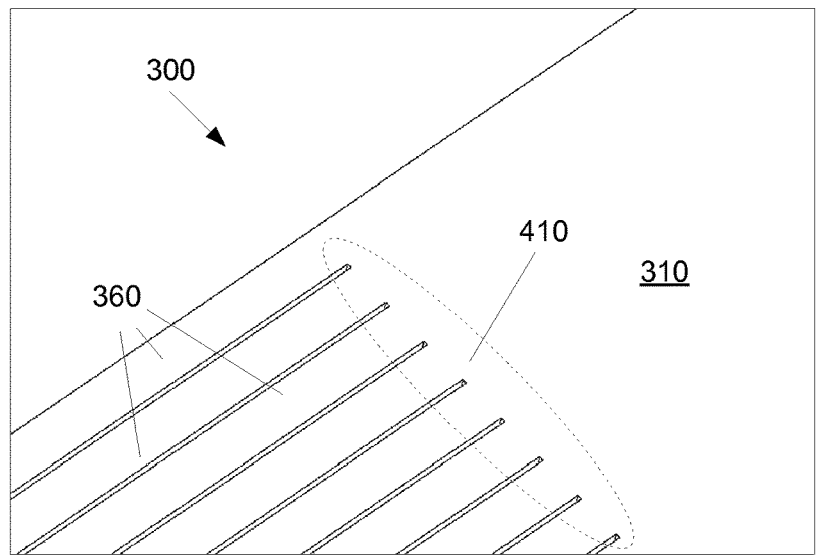
FIGS. 4A, 4B, and 4C are schematic diagrams of the first embodiment of a flexible optic patch.

FIG. 4A shows a flexible patch 300 with a detail of an interface area 410 between the panel 310 portion and the fibrous appendages 360. It may be desirable to bind and/or otherwise treat the interface area 410 to ensure the fissure between individual fibrous appendages 360 does not extend into the panel 310 portion, for example, as a result of a force being applied to one or more of the fibrous appendages, or due to a force on the panel 310 portion. Such binding and/or treating may apply strain relief methods known to persons having ordinary skill in the art.

Figure 4B:
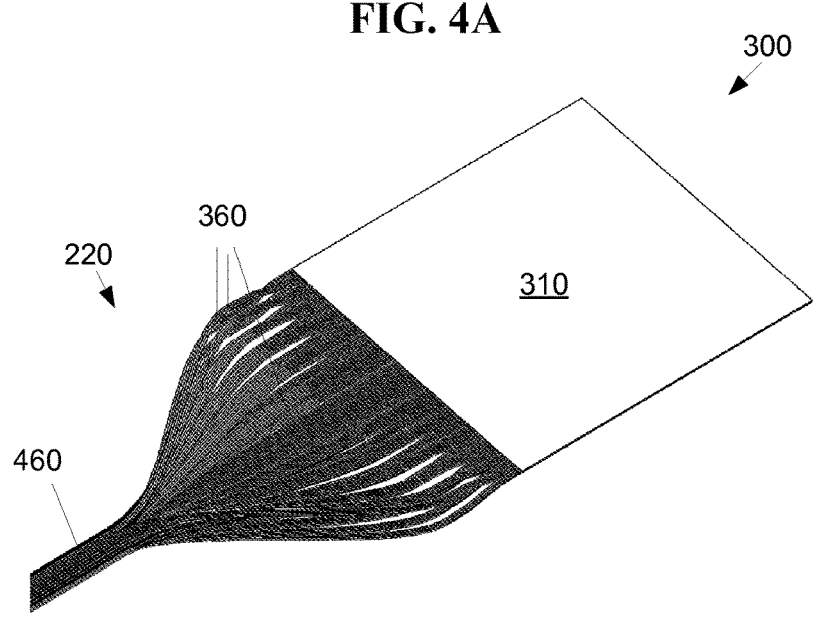

FIG. 4B shows the flexible thin film optic device 300 where the fibrous appendages 360 have been bundled together in a substantially tubular bundle 460. The bundle may be sheathed, for instance in a covering 480 (FIG. 4C) to maintain the bundle as a cable to run the fibrous appendages to the light source 230 (FIG. 2). Such flexible coverings for fiber optic bundles are well known. When the fibrous appendages 360 are long in relation to the size of the panel 310, bundling the fibrous appendages 360 may be advantageous for ease of routing the fibrous appendages 360 between the panel 310 and a light source 230 (FIG. 2). For example, the bundled fibrous appendages 360 may have flexibility in more directions than the panel 310 (FIG. 4A).

Similarly, fibrous appendages 360 may be more flexible and provide additional handling benefits over, for example, wide flat legs attached to the panel 310. While the fibrous appendages 360 may provide more degrees of freedom regarding the direction of flexibility, it should be noted that a sharp bend of one or more of the fibrous appendages 360 may defeat the TIR of the lightguide material, allowing at least some light to escape the fibrous appendages. The TIR of the fibrous elements 360 and the panel 310 depends on several factors, for example, the material the fibrous elements 360 and the panel 310 are made from, the geometry of how the fibrous elements 360 and the panel 310 are formed and arranged, the smoothness of the surface of the fibrous elements 360 and the panel 310, and the optical qualities of any coating or laminate applied to the fibrous elements 360 and the panel 310. The smoothness of the surface may be adjusted by polishing, for example, mechanical polishing, thermal treating, and/or chemical treatments.

The maximum bend of a lightguide material is typically measured by the minimum bend radius of the material, in this case, the flexible panel 310 and/or the fibrous elements 360. The minimum bend radius of the lightguide material may be determined according to Eq. 1, $$r_{min} = m/((n^* \cos \alpha) - 1) \qquad \text{Eq. 1}$$

where $r_{min}$ is the minimum bend radius, m is the thickness of the material, $\alpha$ is the ingress light collimation angle, and n is the material index of refraction.

The individual strands of fibrous appendages 360 in a bundle 460 may be organized in a specific order, such that the relationship between an individual strand and an illuminated portion of the panel 310 is known. Alternatively, the bundle may be haphazardly ordered. The strands in the bundle 460 may be arranged for stability, for example, in a spiral or a weave. The fibrous appendages 360 may be bundled together into a single bundle 460, or into two or more bundles.

The flexible panel 310 and/or the conduit 220 are formed of a light conducting material, for example, polycarbonate, that efficiently conducts light from the light source 230 (FIG. 2) to the flexible panel 310 at the wound 260 (FIG. 2), while not conducting heat generated by the light source 230 (FIG. 2) to the flexible panel 310 at the wound 260 (FIG. 2). Locating the light source remotely from the flexible panel 310 and the wound 260 (FIG. 2) allows for incorporation of hotter higher power and higher intensity light sources 230 (FIG. 2) than would be possible with bandages incorporating light sources directly illuminating the wound 260 (FIG. 2).

Other materials may also be chosen for the flexible panel 310 for other properties, for example, gas permeability, and/or steam, or Ethylene Oxide sterilization. Such a material may include, for example, a 4-methylpentene-1 based polyolefin. Such materials may be desirable due to their chemical resistance, which is better than that of polycarbonate and acrylic. Gas permeability may be desirable to allow oxygen flow to and/or from the wound. Autoclavability is desirable to maintain a sterile environment in the vicinity of the wound.

Light sources, such as OLEDs, are difficult to sterilize as their inherent organic compounds degrade, as sterilization methods are designed to break down organic compounds. Sterilization procedures include exposure to gamma radiation, steam autoclave, and Ethylene Oxide (EtO) sterilization. A wider range of low cost materials that may withstand these sterilization techniques are available for the patch and light conduit than for light sources. For example, polymers, which are chosen to be generally resistant to levels of gamma radiation used for sterilization, may be used for the patch and light conduit.

Returning to FIG. 2, the patch 210 may include elements of a conventional wound dressing that act to affix the flexible panel 310 (FIG. 4B) in the vicinity of the wound 260. For example, the patch 210 may include gauze, adhesive tape, cloth, elastic, and other components of a conventional bandage. The patch 210 may include one or more apertures for the light conduit 220 to pass through, thereby conducting light between the light source 230 and the flexible panel 310 (FIG. 4B) within the patch 210.

Figure 4C:
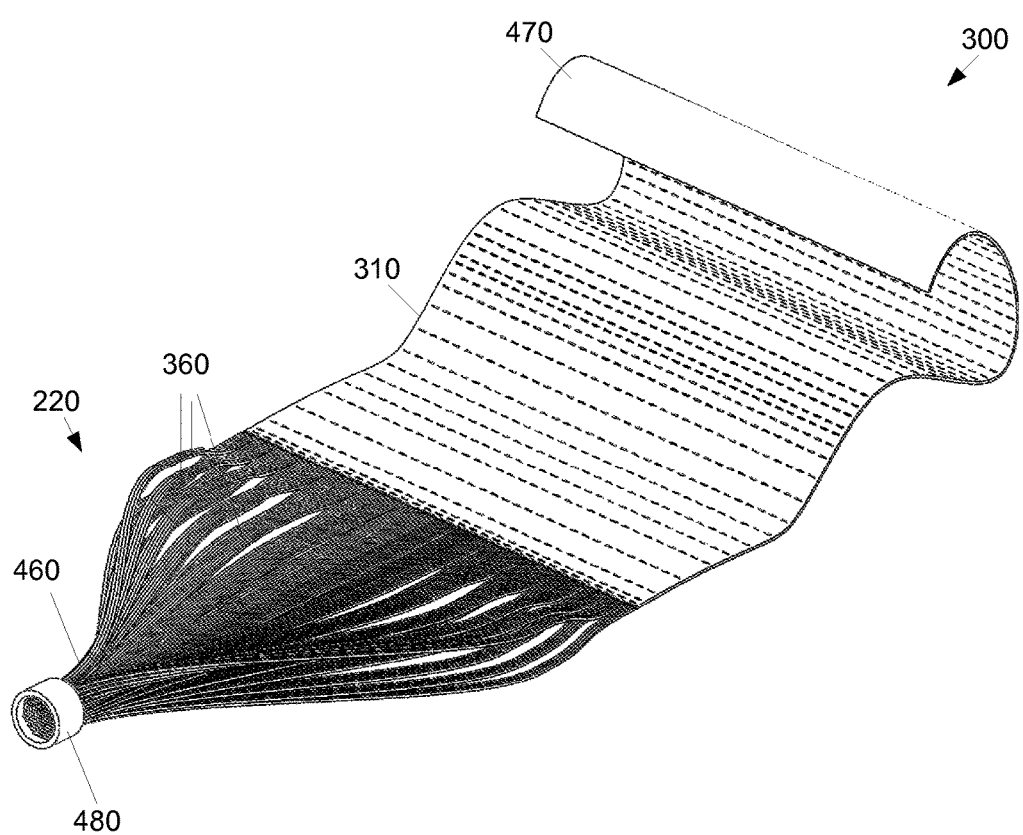

FIG. 4C shows a view of the flexible panel 310 more clearly depicting the flexibility of the panel 310. The panel 310 may include a backing layer 470, mechanically attached to the panel 310. The backing layer 470 may be a transparent gas permeable biocompatible diffuser, for example, applied to the panel 310 with an adhesive. The backing layer 470 may be formed of a gas permeable, sterilizable transparent material, for example, to assist in dispersion of light from the panel. The backing layer 470 may also serve to bind two or more flexible panels 310 together into what functions as a single panel. Similarly, the backing layer 470 may bind together a plurality of thin panels 310 into a single, wider panel.

Figure 12:
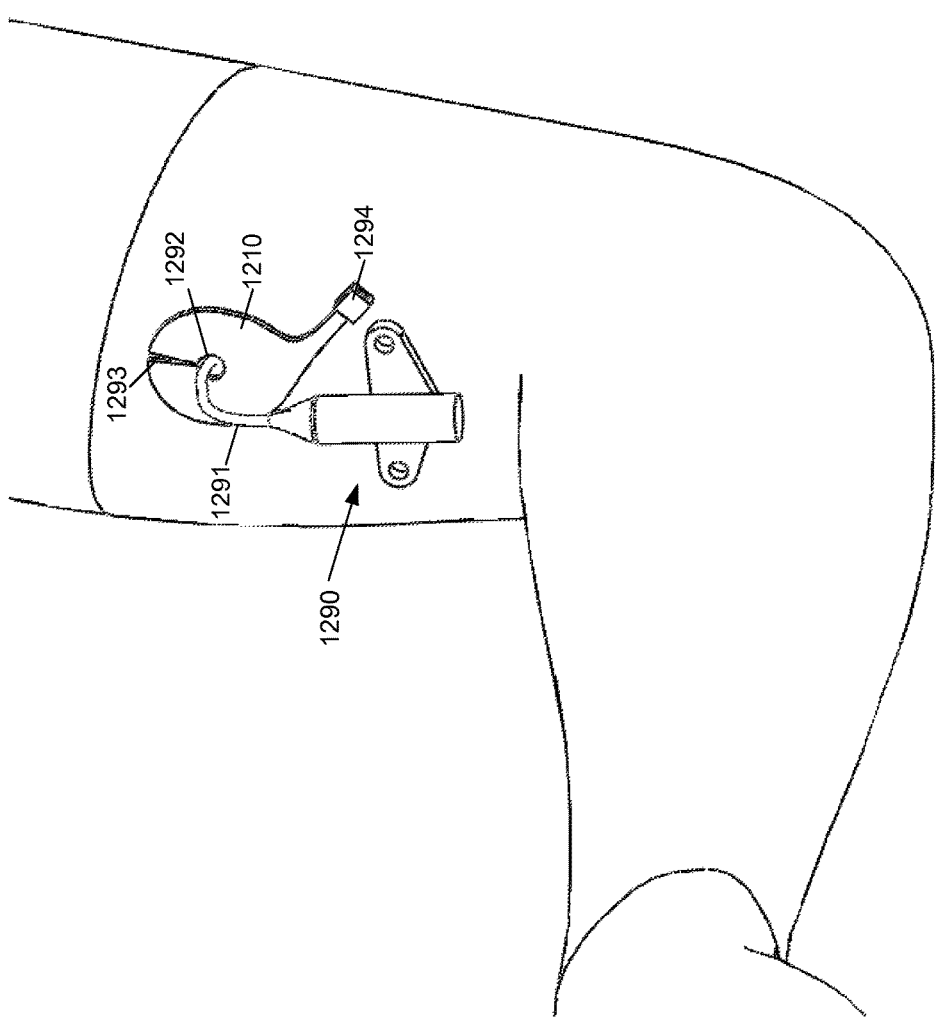
FIG. 12 is a schematic diagram of a flexible optic patch configured to accommodate a catheter or negative pressure apparatus.

As shown by FIG. 12, a panel 1210 may include one or more apertures 1292 so as to provide access to the wound site for other medical devices, for example, a catheter 1290. Such an aperture 1292 may be formed as a shaped hole, for example, a round or oval shaped hole, and/or may be formed as a slit 1293 in the flexible material that allows for a catheter 1290 or similar device to be inserted through the slit 1293 in the panel, thereby deforming the flexible panel 1210 while the catheter tube 1291 is inserted there through. Such a configuration may be advantageous as the slit 1293 provides minimal optical disruption of light through the panel 1210 at times when the catheter 1290 is not being used, yet still provides access to a catheter 1290 without having to replace the patch with another patch having an aperture. As shown by FIG. 12, the panel 1210 may be a non-rectilinear shape. The panel 1210 is attached to a light conduit (not shown) via an optical coupler 1294.

Figure 5:
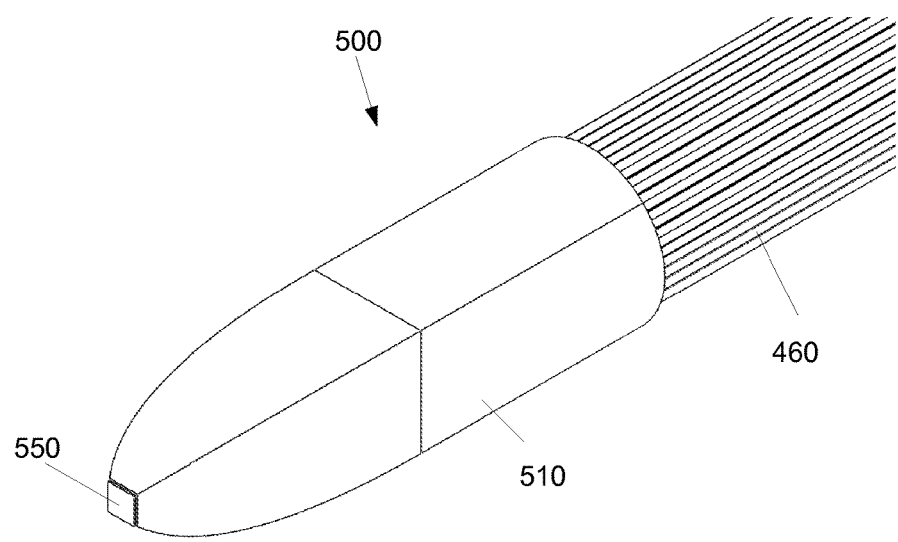
FIG. 5 is a schematic diagram of a light source interface with the first embodiment of a flexible optic patch.

As shown by FIG. 5, the light conduit, in this case, bundle 460, may be connected to a light source 500 such as a CPC (compound parabolic concentrator, or compound parabolic collector) 510. The light source 500 introduces light into the end of one or more fibrous appendages 360 (FIG. 4B) in the bundle 460. The light source 500 may include a radiation emitting element 550, such as an LED. The CPC optic 510 may distribute light from the light source 550 substantially evenly so that each of the strands of the fiber bundle transmits a similar intensity of light. However, there is no objection to a light source where light is unevenly distributed across the individual strands of the bundle 460.

Any means of introducing light into the fibrous appendages 360 (FIG. 4A) is permissible. The illuminating element introducing light into the fibrous appendages 360 may be of any suitable type including for example, but not limited to, incandescent, halogen, xenon, metal-halide, light emitting diodes (LED) including organic light emitting diodes (OLED) and polymer light emitting diodes (PLED), fluorescent, solid state lasers, so-called "remote-phosphors" excited by LEDs or lasers, and plasma light sources. The illuminating element may introduce light directly into the fibrous appendages 360, or may indirectly introduce light into the fibrous appendages 360, for example, using a reflecting element, refracting or a diffusing element.

While the light source 500 in FIG. 5 is shown in an interface with a bundle 460 having substantially round cross section, there is no objection to a light source 500 having other shaped cross sections. The bundle 460 may have a substantially circular cross sectional shape, or may assume other shapes as desired, for example, a square, a rectangle, or a thin and wide ribbon. For example, the bundle may be relatively thin, such as between two and five strands deep, such that the bundle maintains a substantially flat profile. The profile of the bundle 460 may be variable, for example, substantially flat in a first portion, and substantially cylindrical in a second portion, to facilitate positioning and bending.

Figure 6:
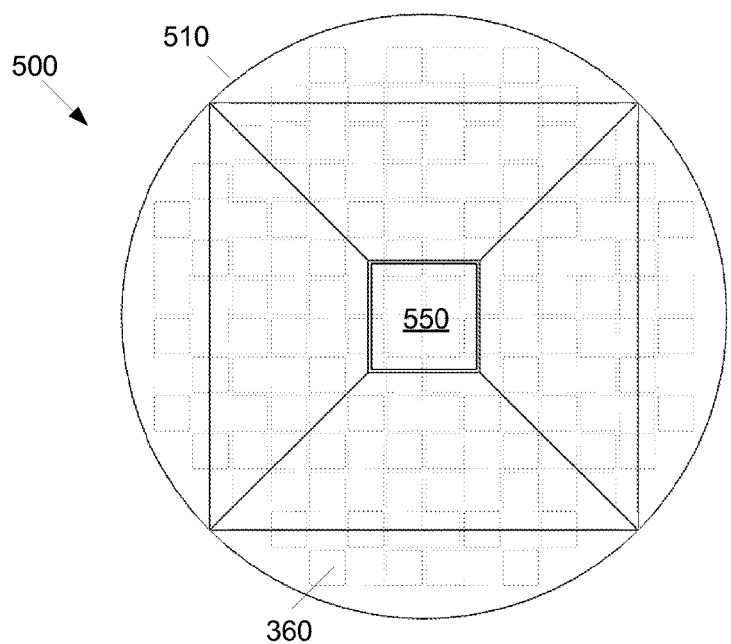
FIG. 6 is a schematic diagram cross section view of a light source interface with the first embodiment of a flexible optic patch.

As shown by FIG. 6, the fibrous appendages 360 may be arranged in patterns according to the configuration of the light source interface. The CPC optic 510 provides both direct light from the illuminating element 550, and light reflected from the internal surface of the CPC optic 510 to the fibrous appendages 360. The fibrous appendages 360 in FIG. 6 each have a substantially square cross section. A rectangular profile of the fibrous appendages 360 may provide an advantageous packing factor, for example, so there are not gaps between strands and where illumination from the light source 500 may be lost. In addition, a rectangular profile for a TIR is a tiling shape so it mixes light. It should be noted that the CPC optic 510 is merely one example of a light source 500, and many other light source configurations are acceptable for use with the thin film optic device 300.

As mentioned above, the fibrous appendages 360 may be bundled together into a single bundle 460, or into two or more bundles. Each bundle 460 may receive light from a separate light source. Indeed, there is no objection to a separate light source being used to provide light to a single strand. In an alternative embodiment, an addressed strand may be traced to a specific corresponding portion of the panel, such that directing light into the addressed strand will cause light to be emitted from the specific corresponding portion of the panel. Each light source may produce a fixed range of wavelengths, or may produce a changeable, controllable range of wavelengths. If multiple light sources are used, they may each be of the same type, or may be of different types.

The light source(s) is optimized to produce radiation/light that is harmful to undesirable flora at the wound site, but otherwise not harmful to the patient. For example, radiation centered at approximately 405 nm, with a bandwidth of approximately 20 nm, has been shown to be effective in killing many organisms, including, but not limited to, *staphyloccus aureus, clostridium perfringens, clostridium difficile, enterococcus faecalis, staphyloccus epidermidis* (CONS), *staphyloccus hyicus* (CONS), *streptococcus pyogenes, listeria monocytogenes, bacillus cereus, mycobacterium terrae, acinetobacter baumannii, pseudomonas aeruginosa, klebsiella pneumonia, proteus vulgaris, escherichia coli, salmonella enteritidis, shigella sonnei, serratia* spp, *aspergillus niger, candida albicans*, and *saccharomyces cerevisiae*.

Different levels of intensity of the light source may be used. In general, the maximum practical irradiance of the patch upon wound should be less than 750 mW/cm$^2$, as this level may cause skin damage. Other considerations may include, for example, safety regulations requiring an irradiance limit of 200 mW/cm$^2$. Irradiances in the range of 10 mW/cm$^2$ to 30 mW/cm$^2$ have been shown to be effective, although lower irradiances would also affect pathogenic organisms. However this embodiment is not limited to these ranges.

Returning to FIG. 4C the panel 310 may typically have a uniform thickness, for example, on the order of 0.010 to 0.8 mm thick, although other thicknesses are permissible. As noted previously, the panel 310 is made from a material acting as a lightguide, for example, a polycarbonate sheet film. The panel 310 may be laminated or coated with another material, for example, a transparent material. The panel 310 may be layered upon an opaque surface, such as metal foil or plastic, or the panel 310 may be layered upon a transparent surface, for example a second panel 310. Such an arrangement may be used to provide two different types of disinfecting light simultaneously.

As mentioned previously, light may be introduced to the panel 310 through the edge, and in particular, through the fibrous appendages 360. Light is caused to be emitted from the planar face of the panel 310 by disrupting the surface of the panel 310. The disruption may be caused by scratching, scuffing, or otherwise deforming the surface of the panel 310. The surface disruption of the panel 310 may be a physical disruption, a chemical disruption, or otherwise. For example, the planar surface of the panel 310 may be disturbed by abrading it, scratching it, sand blasting it, or printing upon the panel with a light disturbing material, for example, a clear or colored epoxy or reflective ink.

The disruption on the planar surface of the panel 310 may be uniform, for example, if a uniform intensity of light is desired. The surface of the panel 310 may be disrupted in some portions, to allow the light to escape from the disrupted portions and not disturbed in other portions of the panel 310. Disrupted portions of the panel 310 may be unequally disrupted such that a first disrupted portion emits more light than a second disrupted portion.

Figure 7:
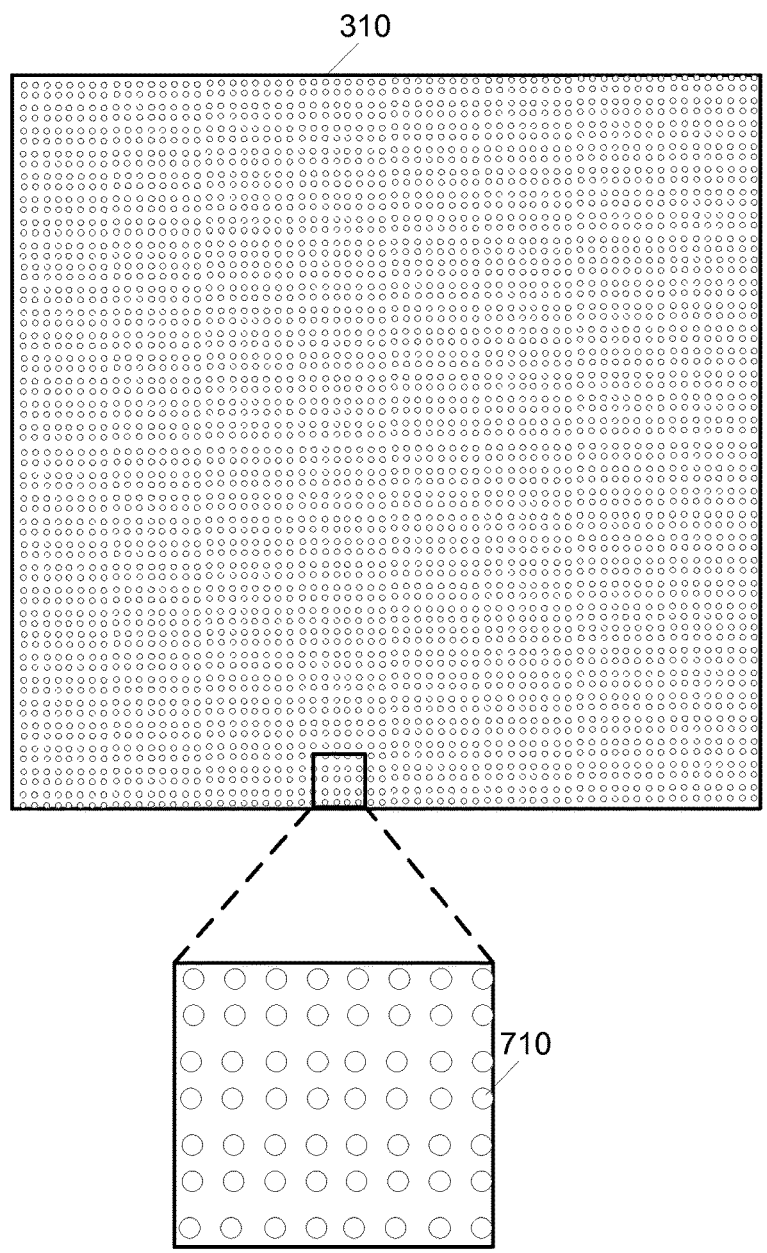
FIG. 7 is a schematic diagram of a detail of the first embodiment of a flexible optic patch.

As shown by FIG. 7, the disruption on the planar surface of the panel 310 may be formed by deforming the material of the panel 310, for example, adding inset dimples or protruding domes 710. The distribution of irradiance emitted from the panel 310 may be changed in several ways, for example, changing the size, shape, and/or density of the domes 710. The disruption may be on the near surface of the panel 310, and/or on the far surface of the panel 310. In the case of the disruption being on the far surface of the panel 310, the viewer observes the emitted light as transmitted through the panel 310.

Figure 8:
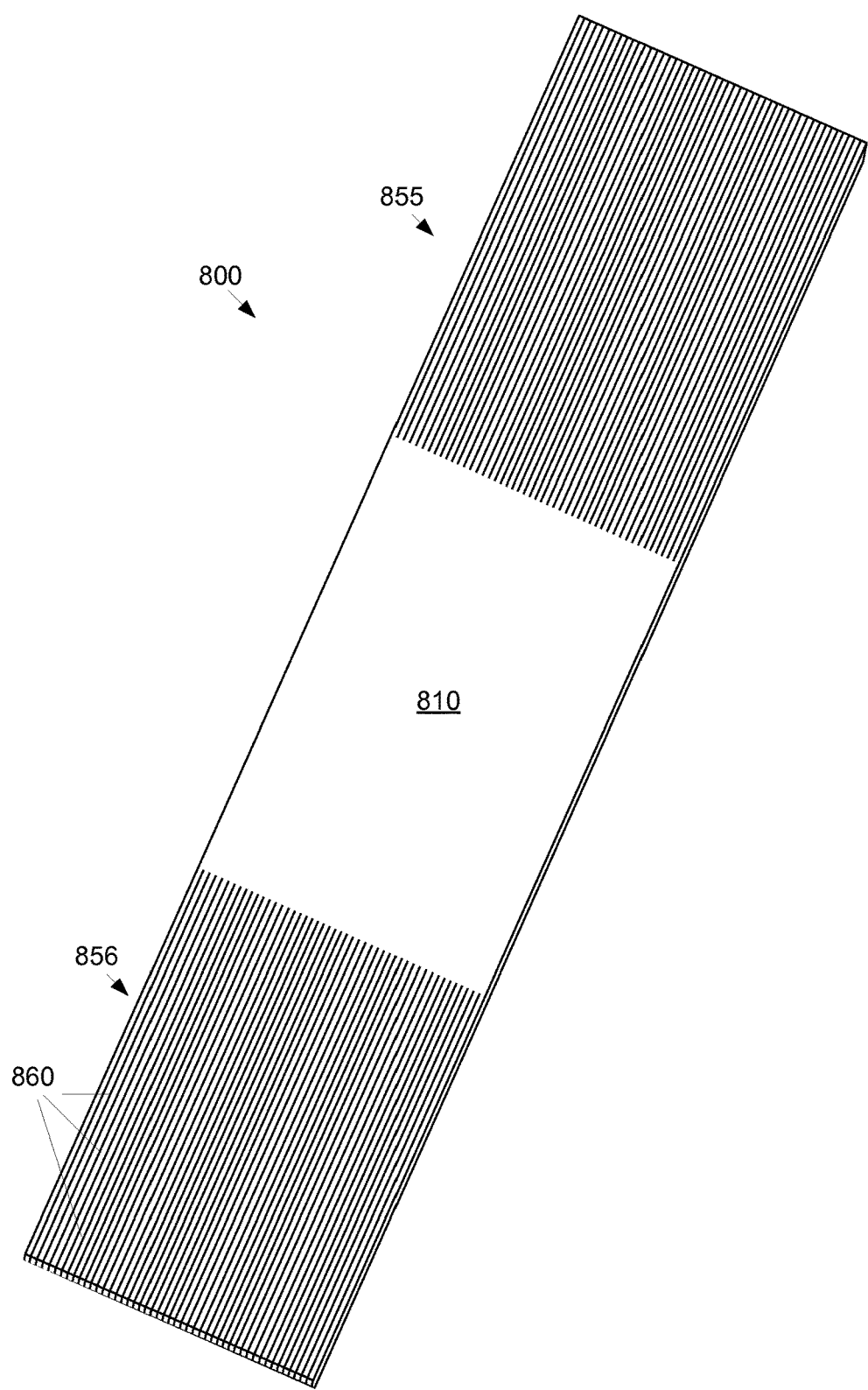
FIG. 8 is a schematic diagram of a second embodiment of a flexible optic patch.

As shown by FIG. 8, a second exemplary embodiment of a flexible emitting area 810 includes a one-piece integral emitting area 810 contiguous with at least two skived regions 855, 856. Each skived region 855, 856 includes a plurality of fibrous appendages 860, where the fibrous appendages 860 are skived from the sheet of material forming the emitting area. Two or more skived regions 855, 856 may be advantageous, for example, for a large emitting device 800, so that light sources may be positioned nearer to light emitting regions of the panel 810. Two or more skived regions 855, 856 may also allow more light sources to be used, providing greater output illumination levels from disturbed areas in the emitting area 810.

Figure 9:
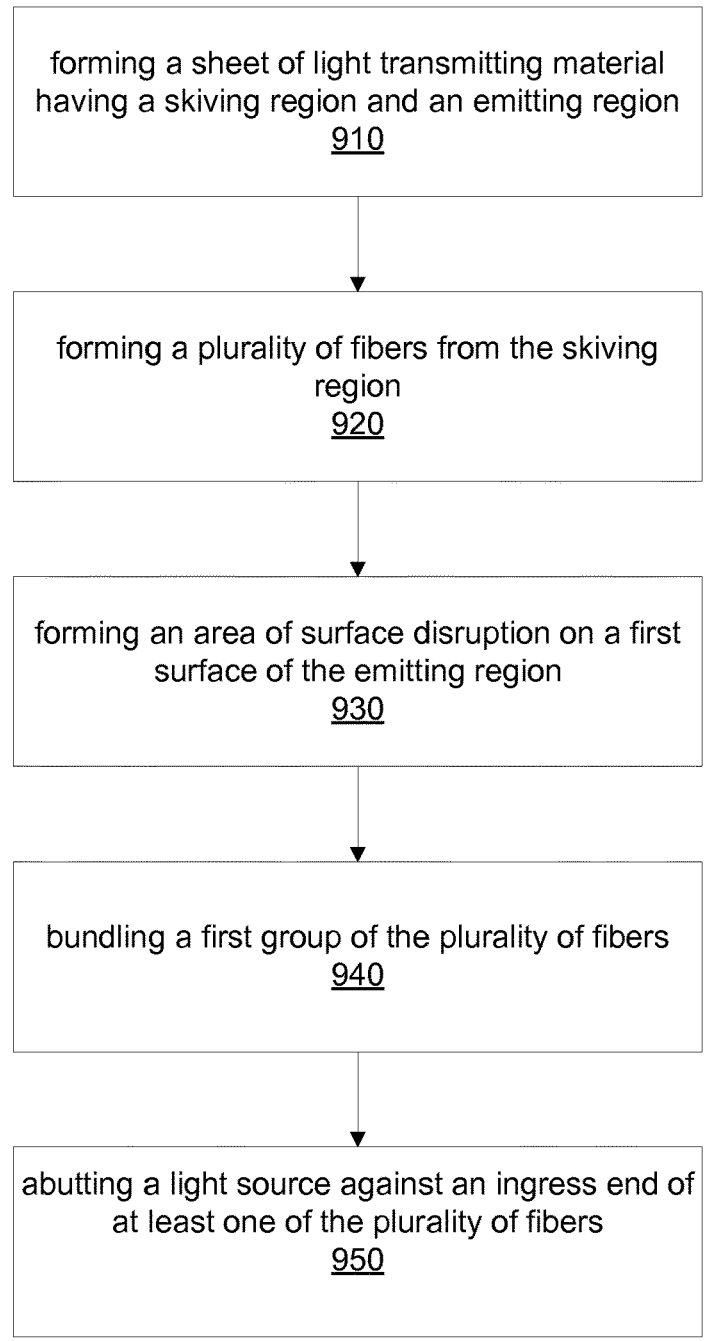
FIG. 9 is a flowchart of an exemplary method for manufacturing a flexible optic patch.

FIG. 9 is a flowchart 900 of an exemplary method for manufacturing a flexible panel and optical conduit of a photo-disinfection patch. It should be noted that any process descriptions or blocks in flowcharts should be understood as representing modules, segments, or steps that include one or more instructions for implementing specific functions in the process, and alternative implementations are included within the scope of the present invention in which functions may be executed out of order from that shown or discussed, including substantially concurrently or in reverse order, depending on the functionality involved, as would be understood by those reasonably skilled in the art of the present invention.

A sheet of light transmitting material having a skiving region and an emitting region is formed, as shown by block 910. The sheet is formed of a suitable lightguide material, for example, polycarbonate. A plurality of fibers is formed from the skiving region. The emitting region and the skiving region may be formed as a continuous sheet, as shown by block 920, such that the individual fibers are formed by cutting or skiving the sheet material in the skiving region into fibers. Or the material in the skiving region may be formed as fibers, for example, by molding the lightguide material into individual fibers contiguous with the emitting region.

An area of surface disruption is formed on a first surface of the emitting region, as shown by block 930. The first surface is typically a flat planar surface, and may be, for example, the planar surface nearest to a wound, or the planar surface farthest from the wound. The disruptions are used to defeat the TIR of the lightguide material, such that light transmitted through the lightguide material, for example, light transmitted into the end of the emitting region, is emitted from the area of surface disruption. The disruptions may be effected in many ways, for example, etching, painting, scratching and depressing the surface.

A first group of the plurality of fibers is bundled into a group, as shown by block 940. The bundle may contain as few as one fiber, or as many as all of the fibers, and may be formed into a shaped bundle to facilitate handling the fibers, for example, in a rope configuration. A light source may be abutted against a detachable ingress end of at least one of the plurality of fibers, as shown by block 950. The light from the light source enters the end of the fiber, and may then be transmitted through the fiber to the emitting region, where the light may be emitted through the area of surface disruption and onto the wound.

Figure 10:
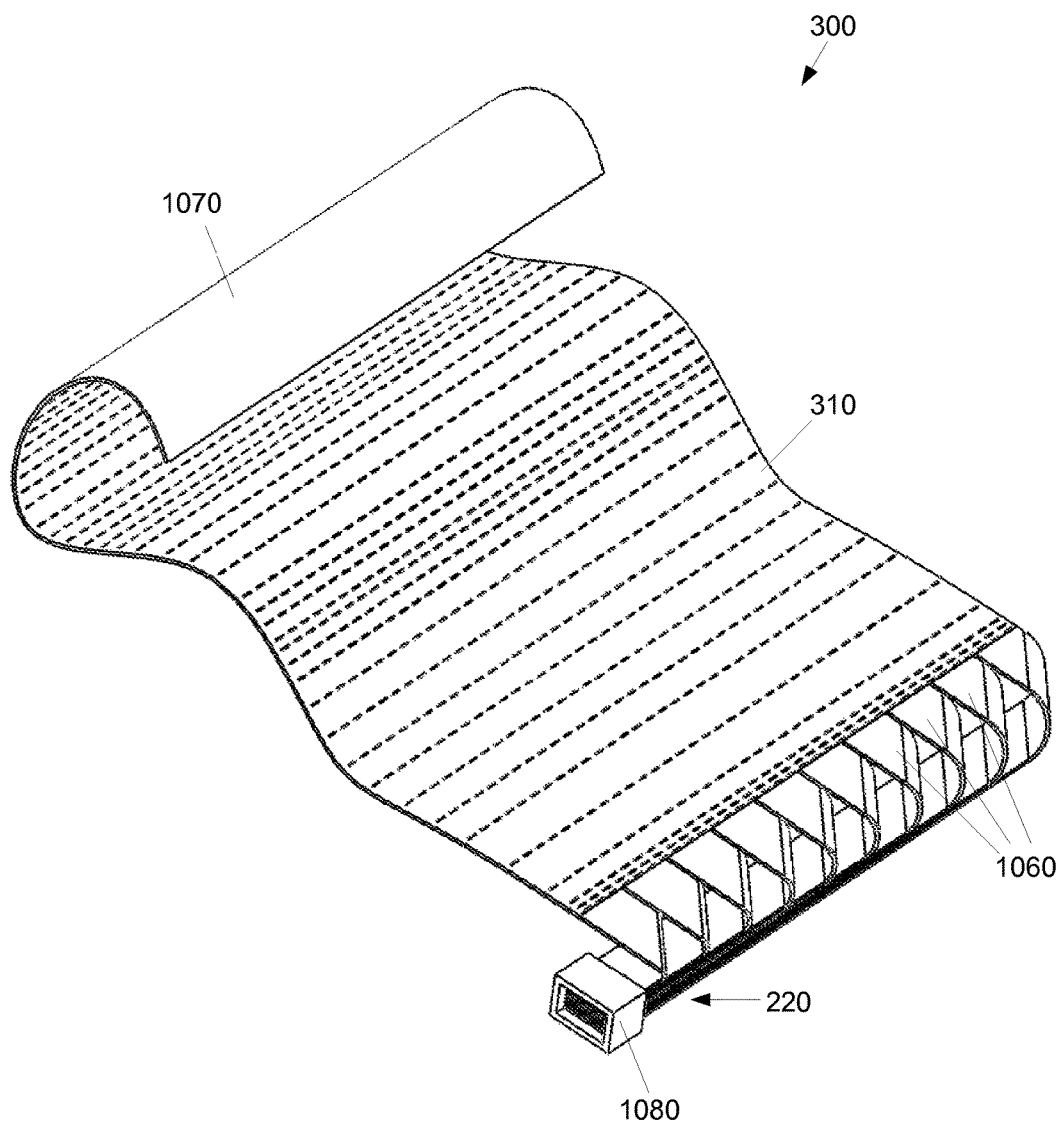
FIG. 10 is a schematic diagram of a third exemplary embodiment of a flexible optic patch.

FIG. 10 depicts a third exemplary embodiment of a flexible thin film optic device 300 where a plurality of ribbons 1060 are used in place of the fibrous appendages 360 (FIG. 4C) of the first embodiment and the second embodiment (860 FIG. 8). The ribbons 1060 are typically wide and thin, such that the width of the ribbon 1060 is greater than the thickness of the ribbon 1060. The thickness of the ribbon 1060 is substantially the same as the thickness of the panel 310. The lengths of the ribbons 1060 may be uniform, or may be non-uniform to facilitate angular bends, as shown in FIG. 10. The ribbons 1060 may provide more flexibility than the panel 310, but will be generally less flexible than the fibrous appendages 360 (FIG. 4C) of the first embodiment and the second embodiment (860 FIG. 8).

While each of the ribbons 1060 is depicted in FIG. 10 as having the same width, there may be embodiments where individual ribbons 1060 have different widths. The ribbons 1060 may be formed with the panel 310 from a single sheet of flexible lightguide material, such that the ribbons 1060 are skived from the sheet and remain attached to the panel 310. Alternatively, the ribbons 1060 may be formed separately, and then physically attached—to the panel 310 using techniques familiar to a person having ordinary skill in the art.

The ribbons 1060 may be layered together in a bundle to form a light conduit 220. The light conduit 220 may be sheathed, for instance in a heat shrink tubing to contain the ribbons 1060 as a cable to run the layered ribbons 1060 to detachable optical coupling 1080. When the ribbons 1060 are long in relation to the size of the panel 310, bundling the ribbons 1060 may be advantageous for ease of routing the ribbons 1060 between the panel 310 and a detachable optical coupling 1080.

The panel 310 may include a backing layer 1070, mechanically attached to the panel 310. The backing layer 1070 may be a transparent gas permeable biocompatible diffuser, for example, applied to the panel 310 with an adhesive. The backing layer 1070 may be formed of a gas permeable, autoclavable (sterilizable) transparent material, for example, to assist in dispersion of light from the panel. The backing layer 1070 may also serve to bind two or more ribbons 1060 together into what functions as a single panel 310.

Figure 11:
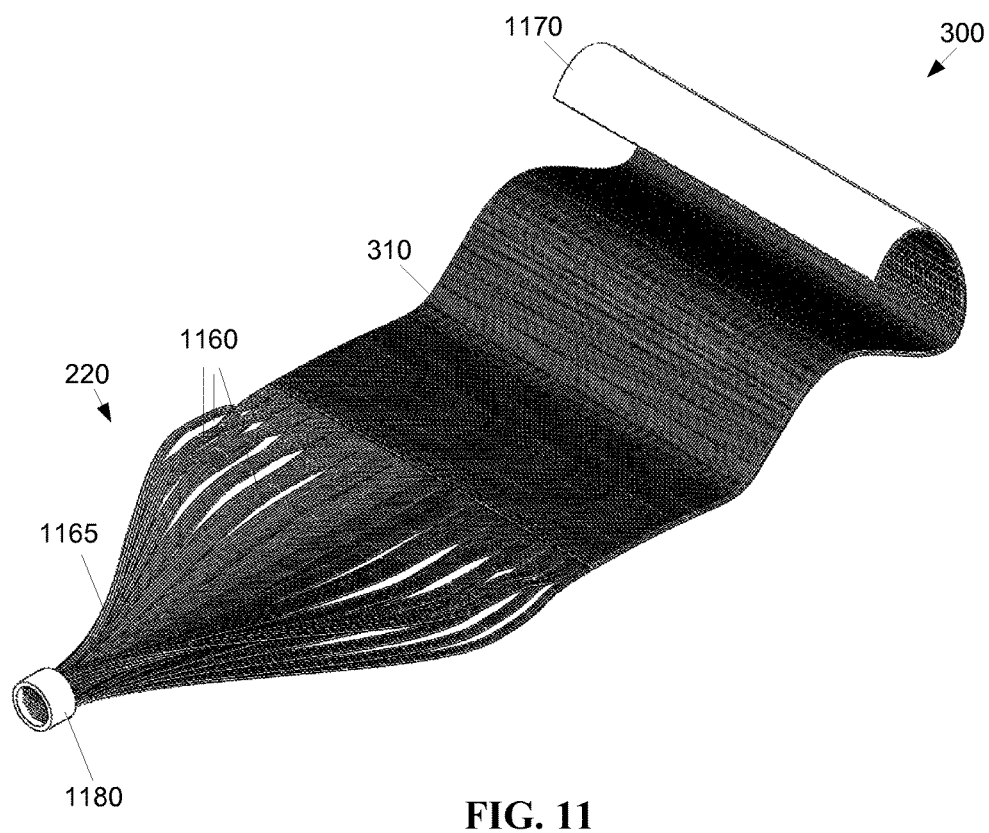
FIG. 11 is a schematic diagram of a fourth exemplary embodiment of a flexible optic patch.

FIG. 11 depicts a fourth exemplary embodiment of a flexible thin film optic device 300 formed from a plurality of optical fibers 1160 that are physically aligned and mechanically attached, for example, with a transparent adhesive backing layer 1170. The surfaces of individual optical fibers 1160 may disturbed in the panel 310 region, allowing light introduced into the fibers 1160 by a light source 210 (FIG. 2) to be emitted from the fibers 1160 in the area of the wound 260 (FIG. 2). The optical fibers 1160 may be gathered together in a bundle 1165 to form a light conduit 220. The light conduit 220 may be sheathed, for instance in a heat shrink tubing to contain the optical fibers 1160 as a cable to run the optical fibers 160 to the light source 230 (FIG. 2). A detachable optical coupling 1180 may be used to detachably couple the light conduit 220 from the light source 230 (FIG. 2).

The backing layer 1170 binds the optical fibers 1160 together into what functions as a single panel 310. The backing layer 1170 may be a transparent gas permeable biocompatible diffuser, for example, applied to the panel 310 with an adhesive. The backing layer 1170 may be formed of a gas permeable, autoclavable (sterilizable) transparent material, for example, to assist in dispersion of light from the panel 310. The optical fibers 1160 each have a substantially square cross section. Alternatively, the optical fibers 1160 may have other shaped cross sections, for example, circular or elliptical shaped cross sections.

A flexible light bandage may incorporate one or more apertures to allow vacuum drawn fluid to pass through it, allowing use of a NPWT device, combining light therapy with a negative pressure wound therapy for use in wounds, for example, burns, with high risks of infection.

Figure 13:
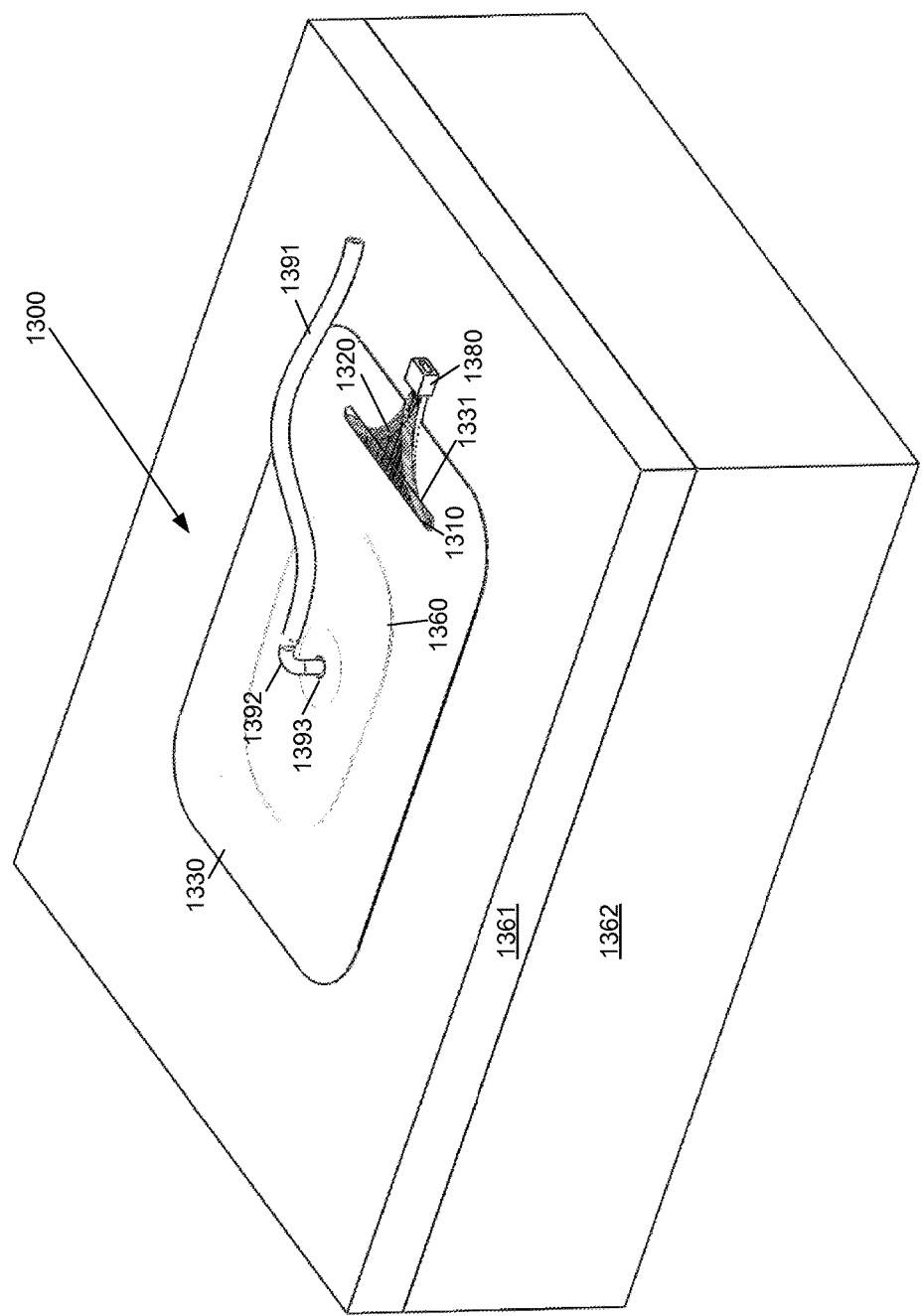
FIG. 13 is a schematic diagram of a negative pressure wound therapy device providing patient safe light to a wound.

In a fifth, a sixth, and a seventh exemplary embodiment, an NPWT device (or dressing) incorporates a flexible light transmitting panel. As shown by FIG. 13, these embodiments include a wound dressing 1300 in and around a wound 1360. The wound may be disposed in surface tissue 1361 and extend into deep tissue 1362 of a patient. The dressing 1300 includes an open cell foam 1420 (FIG. 14) fitted to the contours of the wound 1360. The overlying open cell foam 1420 (FIG. 14) may be covered with a non-adherent dressing film (not shown) and sealed with an adhesive drape 1330. The adhesive drape 1330 may be, but is not limited to be transparent or translucent. A vacuum port 1392 is connected to the open cell foam 1420 (FIG. 14) dressing through an opening 1393 of the adhesive drape 1330. A vacuum tube 1391 connects the vacuum port 1392 to a vacuum pump or vacuum source (not shown). The adhesive drape 330 seals the wound 1360, providing a controlled, closed environment for removing excess fluid from the wound 1360 to enhance circulation and remove wound fluids.

A flexible light transmitting panel 1310 is incorporated into the dressing 1300. The flexible light transmitting panel 1310 is configured to either directly or indirectly illuminate the wound 1360. A light conduit 1320 formed of one or more light transmitting fibers or films conducts light to the flexible light transmitting panel 1310 from a light source 230 (FIG. 2). The light conduit 1320 may pass through an opening 1331 in the adhesive drape 1330, such that the adhesive drape 1330 seals the wound 1360 area while allowing the light conduit 1320 to pass through the adhesive drape. A detachable optical coupling 1380 may be used to detachably couple the light conduit 1320 from the light source 230 (FIG. 2).

The open cell foam 1420 (FIG. 14) is used to fill or cover the wound 1360, for example, an open cavity wound, and can be cut to size to fit the wound 1360. The open cell foam 1420 (FIG. 14) is applied to substantially fill or cover the wound 1360, and the adhesive drape 1330 is applied over the top of the wound 1360 to seal the area around the wound 1360.

Figure 14:
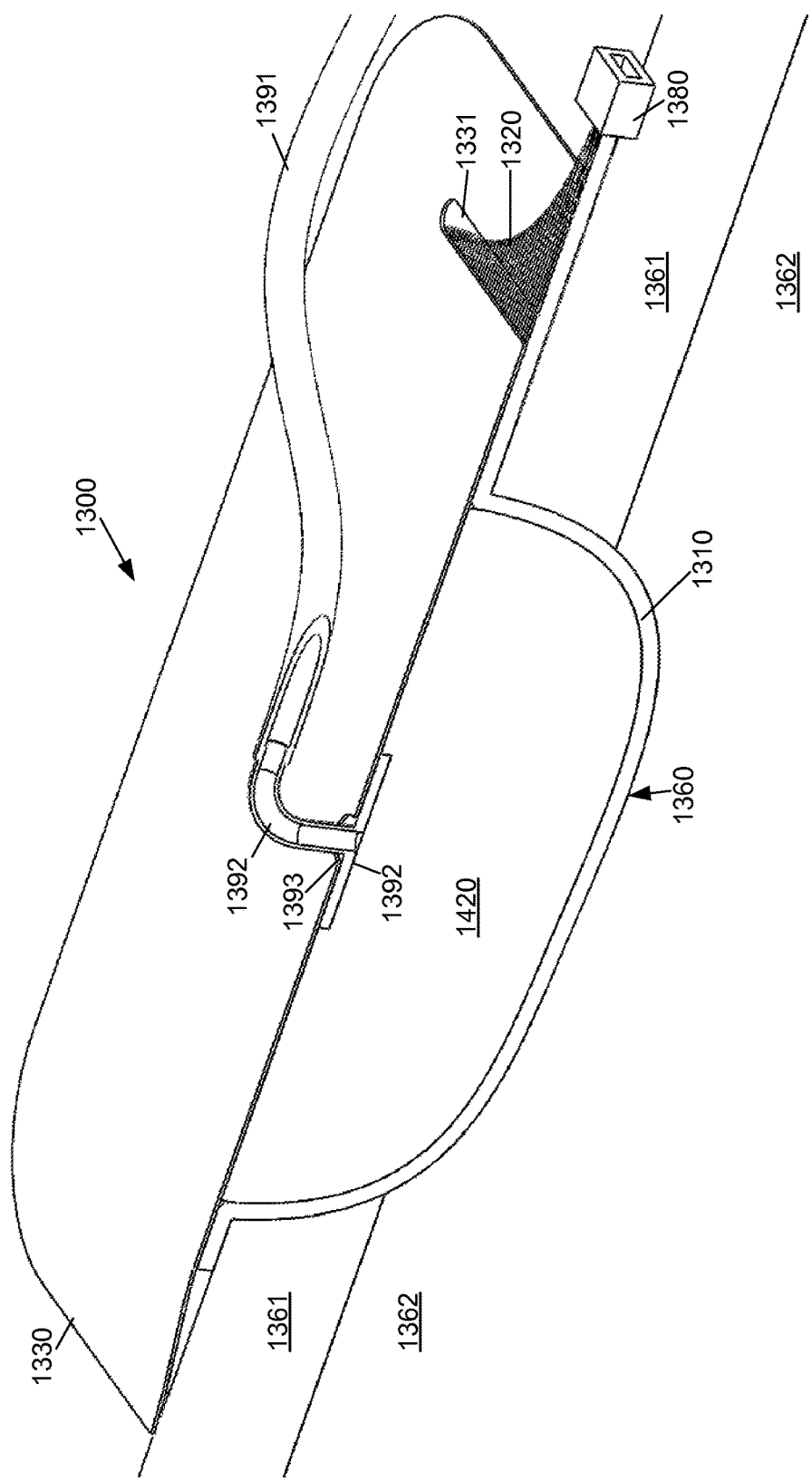
FIG. 14 is a schematic cutaway diagram of a negative pressure wound therapy device providing patient safe light directly to a wound.

As shown in FIG. 14, under the fifth embodiment, the flexible light emitting panel 1310 is form fitted to the contour of the wound 1360, such that the light emitting panel 1310 is substantially adjacent to the wound, and the open cell foam 1420 is packed adjacent to the light emitting panel 1310. The light emitting panel 1310 is configured such that fluid can pass through the light emitting panel 1310 with openings or an open mesh weave of fiber optic elements located adjacent to the wound 1360. The fluid thereafter is drawn by the vacuum to pass through the open cell foam 1420, and into the vacuum port 1392 via the opening 1393 in the sealed adhesive drape 1330. The positioning of the light emitting panel 1310 substantially adjacent to the wound 1360 allows access of light from the light emitting panel 1310 to the wound 1360. A thin layer of material, such as a transparent or translucent dressing (not shown) may be positioned between the light emitting panel 1310 and the wound 1360, for example, to keep the light emitting panel 1310 from adhering to the wound 1360.

Figure 15:
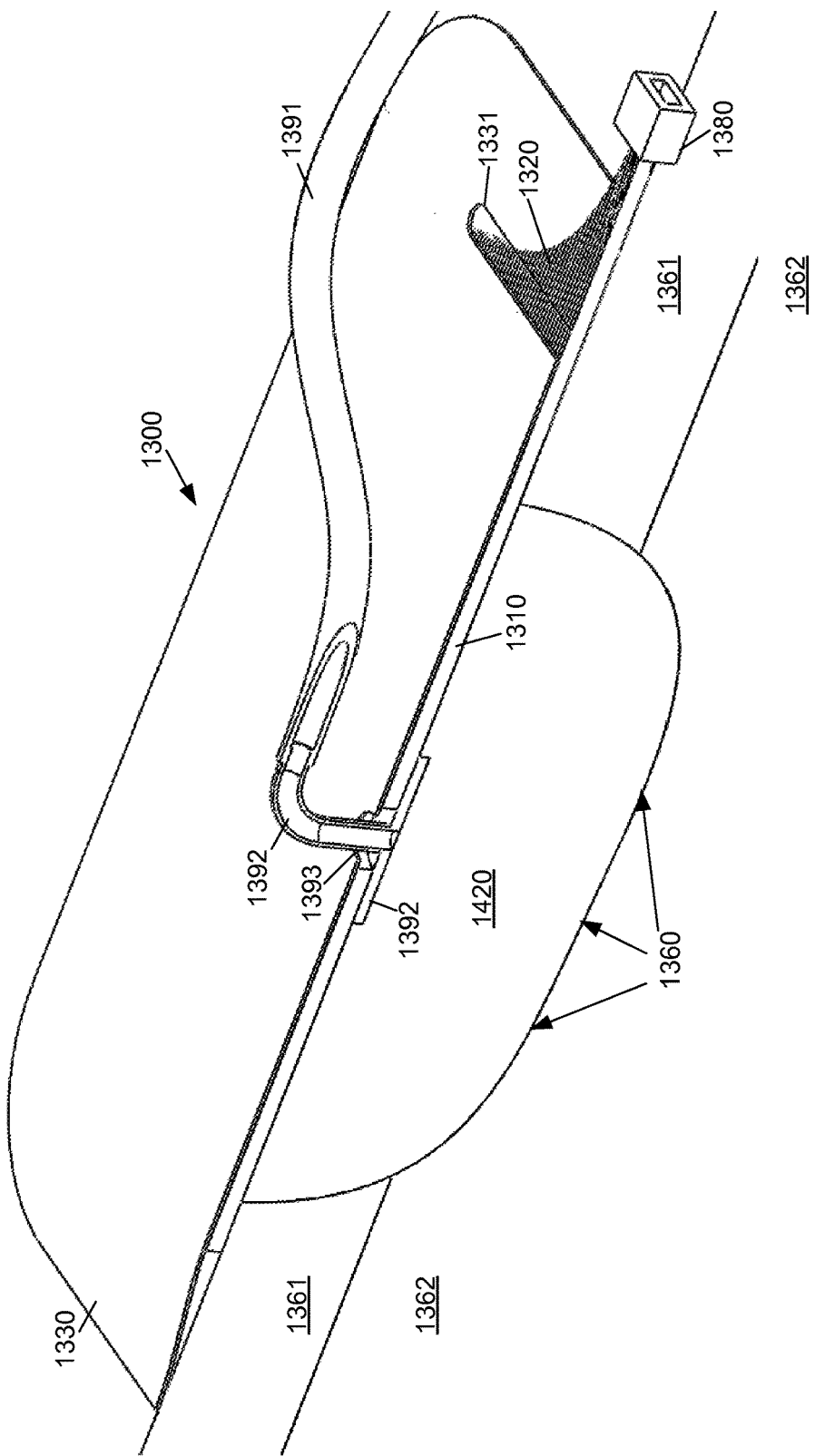
FIG. 15 is a schematic cutaway diagram of a negative pressure wound therapy device providing patient safe light to a wound through an open cell foam dressing material.

As shown in FIG. 15, under the sixth embodiment the open cell foam 1420 is form fitted to the contour of the wound 1360, such that the open cell foam 1420 is substantially adjacent to the wound and the light emitting panel 1310 is adjacent to the open cell foam 1420. The open cell foam dressing 1420 material is at least partially translucent to one or more flora lethal radiation wavelengths of light transmitted by the conduit 1320 to the light emitting panel 1310, so that light from the light emitting panel 1310 may pass through the open cell foam 1420 onto the wound 1360.

Unlike the fifth embodiment, under the sixth embodiment the light emitting panel 1310 may not be configured such that fluid can generally pass through the light emitting panel 1310. The light emitting panel 1310 may include an opening 1393 to facilitate the vacuum port 1392 therethrough only at the location of the opening 1393. The light emitting panel 1310 may not be otherwise permeated to serve as the sealing layer for the vacuum.

If the light emitting panel 1310 serves as the sealing layer for the vacuum, the light emitting panel 1310 includes one or more apertures 1393 for the vacuum port 1392 to physically pass through. In an alternative embodiment, the vacuum port 1392 may not physically pass through the aperture(s) 1393 in the light emitting panel 1310, but instead terminate at an attaching point on the light emitting panel 1310 to substantially surround the aperture 1393 in the light emitting panel 1310.

Other embodiments are possible. Under a seventh exemplary embodiment of a light therapy device 1300, the light emitting panel 1310 may be incorporated into the open cell foam dressing layer 1420. The light emitting panel 1310 may include optical emitting elements incorporated into the open foam dressing layer 1420, for example as a weave of fiber optic elements, a plurality of individual fiber optic elements, or a perforated or otherwise fluid permeable flexible fiber optic panel. The light emitting panel 1310 portion of the open foam dressing layer 1420 may be disposed at or near the surface of the open foam dressing layer 1420, so that the light emitting panel 1310 portion is disposed near to or adjacent the wound 1360 surface. Alternatively, the open cell foam dressing material may be translucent to flora lethal radiation wavelengths, so that the light emitting panel 1310 portion need not be disposed in the immediate vicinity of the wound.

In summary it will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A light conveying device configured to convey light received from a radiation source to a wound, comprising:
   a radiation conduit optically coupled to the radiation source comprising a radiation ingress portion and a radiation egress portion; and
   a flexible panel of radiation transmitting material optically coupled to the radiation conduit, and configured to at least partially conform to a surface contour of the wound,
   the flexible panel formed of a single flexible film of the radiation transmitting material defining a first surface, a second surface opposite the first surface,
   wherein the first surface has a disrupted surface area that causes radiation received from the radiation conduit to be emitted from the first surface toward the wound,
   wherein all of the light that is emitted from the light conveying device toward the wound passes through the first surface of the flexible panel at the disrupted surface area,
   wherein the radiation conduit comprises a plurality of fibrous appendages contiguously extending from the flexible panel,
   wherein the radiation conduit, including the fibrous appendages of the radiation conduit, is integral with the flexible panel such that the radiation conduit and the flexible panel are formed as a single continuous element, and
   wherein the radiation conduit and the flexible panel are formed from the same material and by a process consisting of:
      providing a thin sheet or film of the material that includes a panel portion and a skiving portion; and
      skiving the skiving portion into the plurality of fibrous appendages,
      wherein the panel portion forms the flexible panel of the light conveying device.

2. The device of claim 1, wherein the flexible panel comprises an edge lit film.

3. The device of claim 1, wherein each of the plurality of fibrous appendages comprises a tip configured for radiation ingress into the fibrous appendage.

4. The device of claim 1, wherein the light conveying device further comprises a transparent gas permeable biocompatible laminate mechanically attached to the panel.

5. The device of claim 1, wherein the flexible panel and the radiation conduit are formed from a single flexible film of the radiation conducting material.

6. The device of claim 5, wherein each of the plurality of fibrous appendages has a substantially square cross section.

7. The device of claim 5, wherein a first group of the plurality of fibrous appendages are grouped in a first bundle.

8. The device of claim 7, wherein a second group of the plurality of fibrous appendages are grouped in a second bundle.

9. The device of claim 1, wherein the patch further comprises a negative pressure wound therapy device.

10. The device of claim 1, wherein the radiation conduit is flexible and able to flex independently relative to the flexible panel.

11. The device of claim 1, wherein the radiation transmitting material is able to withstand sterilization by steam or Ethylene Oxide sterilization.

12. The device of claim 1, wherein the device does not include a separate connector between the radiation conduit and the flexible panel, since the radiation conduit is integral with and is formed as a single continuous element with the flexible panel.

13. The device of claim 1, wherein the single flexible film of radiation transmitting material further defines side edges, wherein each of the side edges extends between the first surface and the second surface at an outer periphery of the first surface and the second surface, and wherein the first surface extends continuously, without interruption, to all of the side edges of the flexible panel.

14. The device of claim 1, wherein the material of the flexible panel is not harmed by sterilization.

15. A light conveying device configured to convey light received from a radiation source to a wound, comprising:
   a radiation conduit comprising fibrous appendages, a radiation ingress portion, and a radiation egress portion; and
   a flexible panel of radiation transmitting material optically coupled to the radiation conduit, and configured to at least partially conform to a surface contour of the wound,
   the flexible panel formed of a single flexible film with a first planar surface, a second planar surface, and side edges, wherein each of the side edges extends between the first planar surface and the second planar surface at an outer periphery of the first planar surface and the second planar surface,
   wherein the first surface extends continuously, without interruption, to all of the side edges of the flexible panel,
   wherein the radiation conduit, including the fibrous appendages, is integral with the flexible panel, including the one piece integral light emission area formed of a single flexible film, such that the radiation conduit and the flexible panel are formed as a single continuous element,
   wherein the radiation conduit and the flexible panel are formed from the same material and by a process consisting of:
      providing a thin sheet or film of the material that includes a panel portion and a skiving portion; and
      skiving the skiving portion into the plurality of fibrous appendages,
      wherein the panel portion forms the flexible panel ,of the light conveying device,
   wherein the radiation conduit and the flexible panel are formed of a material not harmed by sterilization, and
   wherein all of the light that is emitted by the light conveying device toward the wound passes through a disrupted surface area on the first planar surface.

16. The device of claim 15, wherein each fibrous appendage has a substantially rectangular cross section.

17. The device of claim 15, wherein a first group of the fibrous appendages is grouped in a first bundle.

18. The device of claim 17, wherein a second group of the fibrous appendages is grouped in a second bundle.

19. The device of claim 15, further comprising the radiation source configured to produce radiation having average emittance from the flexible film less than 750 milliwatts per square centimeter, wherein the flora lethal radiation wavelengths comprise a bandwidth substantially within the range of 400 nm-410 nm.

20. A system providing patient safe light to a wound, comprising:
   a radiation source, producing flora lethal radiation wavelengths;

a radiation conduit optically coupled to the radiation source comprising a radiation ingress portion and a radiation egress portion conveying the floral lethal radiation from the radiation source; and a patch remotely located from the radiation source and optically coupled to the radiation conduit, configured to at least partially conform to a surface contour of the wound comprising:

a flexible panel comprising a one piece integral light emission area formed of a single flexible film of radiation transmitting material not harmed by sterilization, the panel comprising a first planar surface, a second planar surface, and side edges that extend from the first planar surface to the second planar surface at an outer periphery of the first planar surface and the second planar surface, wherein the first planar surface comprises a disrupted surface area configured to emit radiation received from the radiation conduit egress portion toward the wound, wherein the first planar surface extends continuously, without interruption, to all of the side edges of the flexible panel, wherein all of the light that is emitted by the patch toward the wound passes through the disrupted surface area on the first planar surface, and wherein the radiation conduit, including fibrous appendages of the radiation conduit, is integral with the flexible panel, including the one piece integral light emission area formed of a single flexible film, such that the radiation conduit and the flexible panel are formed as a single continuous element, and wherein the radiation conduit and the flexible panel are formed from the same material and by a process consisting of:

providing a thin sheet or film of the material that includes a panel portion and a skiving portion; and skiving the skiving portion into the plurality of fibrous appendages, wherein the panel portion forms the flexible panel of the light conveying device.

21. The system of claim 20, wherein the flora lethal radiation wavelengths comprise a bandwidth substantially within the range of 400 nm-410 nm.

22. The system of claim 20, wherein the flora lethal radiation wavelengths comprise a bandwidth substantially within the range of 380 nm-500 nm.

23. The system of claim 20, wherein a level of the radiation is configured to provide a penetration depth of at least 2 cm through human skin.

24. The system of claim 20, wherein the flexible panel emits a substantially uniform level of illuminance across its length and width.

25. The system of claim 20, wherein the radiation source is configured to produce radiation having average emittance from the flexible film less than 750 milliwatts per square centimeter.

26. The system of claim 20, wherein the radiation has an average emittance from the flexible film between about 50 microwatts per square centimeter and 750 milliwatts per square centimeter.

27. The system of claim 20, wherein the radiation transmitting material is able to withstand sterilization by steam or Ethylene Oxide sterilization.

28. A light conveying device configured to convey light received from a radiation source to a wound, comprising:

a radiation conduit optically coupled to the radiation source comprising a radiation ingress portion and a radiation egress portion; and a patch remotely located from the radiation source and optically coupled to the radiation conduit, configured to at least partially conform to a surface contour of the wound, comprising:

a flexible panel comprising a one piece integral light emission area formed of a single flexible film of radiation transmitting material, the panel comprising a first planar surface and a second planar surface, wherein at least one of the first planar surface and the second planar surface comprises a disrupted surface area configured to emit radiation received from the radiation conduit egress portion upon the wound, wherein the radiation conduit comprises a plurality of fibrous appendages contiguously extending from the flexible film, wherein all of the light that is emitted by the patch toward the wound passes through the disrupted surface area on the first planar surface or the second planar surface, and wherein the radiation conduit, including the fibrous appendages of the radiation conduit, is integral with the flexible panel, including the one piece integral light emission area formed of a single flexible film, such that the radiation conduit and the flexible panel are formed as a single continuous element, and wherein the radiation conduit and the flexible panel are formed from the same material and by a process consisting of:

providing a thin sheet or film of the material that includes a panel portion and a skiving portion; and skiving the skiving portion into the plurality of fibrous appendages, wherein the pane portion forms the flexible panel of the light conveying device.

29. The device of claim 28, wherein the radiation transmitting material is able to functionally withstand sterilization.

* * * * *